United States Patent [19]
Sassanfar et al.

[11] Patent Number: 5,871,987
[45] Date of Patent: Feb. 16, 1999

[54] CANDIDA TYROSYL-TRNA SYNTHETASE PROTEINS, NUCLEIC ACIDS AND STRAINS COMPRISING SAME

[75] Inventors: Mandana Sassanfar; Paul L. Gallant, both of Dedham; Xiaoyu Shen, S. Boston; Nianjun Tao, Malden; Jianshi Tao, North Andover; Fariba Houman, Belmont, all of Mass.

[73] Assignee: Cubist Pharmaceuticals, Inc., Cambridge, Mass.

[21] Appl. No.: 743,130

[22] Filed: Nov. 1, 1996

[51] Int. Cl.$^6$ ............................... C12N 9/00; C12N 1/14; C12N 15/00; C07H 21/04

[52] U.S. Cl. ................. 435/183; 435/252.3; 435/254.11; 435/325; 435/320.1; 536/23.2; 536/23.4

[58] Field of Search ................................. 435/183, 252.3, 435/254.11, 320.1, 325; 536/23.2, 23.4

[56] References Cited

U.S. PATENT DOCUMENTS

| | | | |
|---|---|---|---|
| 4,713,337 | 12/1987 | Jasin et al. | 435/172.3 |
| 4,788,148 | 11/1988 | Nilsson et al. | 435/320 |
| 4,952,501 | 8/1990 | Jasin et al. | 435/69.2 |
| 4,963,487 | 10/1990 | Schimmel et al. | 435/172.3 |
| 5,370,995 | 12/1994 | Hennecke et al. | 435/69.1 |
| 5,561,054 | 10/1996 | Kron et al. | 435/69.1 |

FOREIGN PATENT DOCUMENTS

WO 95/09927  4/1995  WIPO.

OTHER PUBLICATIONS

Jones, M. D. et al., "Natural Variation of Tyrosyl–tRNA Synthetase and Comparison with Engineered Mutants," *Biochemistry*, 25:1887–1891 (1986).

Edwards, H. et al., "An *E. coli* Aminoacyl–tRNA Synthetase Can Substitute for Yeast Mitochondrial Enzyme Function In Vivo," *Cell*, 51:643–649 (1987).

Barker, D. G. et al., "The Tyrosyl–tRNA Synthetase from *Escherichia coli*," *FEBS Letters*, 150(2):419–423 (1982).

Chow, C. M., and RajBhandary, U. L., "*Saccharomyces cerevisiae* Cytoplasmic Tyrosyl–tRNA Synthetase Gene," The Journal of Biological Chemistry, 268(17):12855–12863 (1993).

Leuker, Christoph E. and Ernst, Joachim, "Toxicity of a Heterologous Leucyl–tRNA (anticodon CAG) in the Pathogen *Candida albicans*: In Vivo Evidence for Non–Standard Decoding of CUG Codons," *Mol. Gen. Genet.* 245:212–217 (1994).

Salazar, O. et al., "*Thiobacillus ferrooxidans* Tyrosyl–tRNA Synthetase Functions In Vivo in *Escherichia coli*," *Journal of Bacteriology*, 176(14):4409–4415 (1994).

Racher, K.I. et al., "Expression and Characterization of a Recombinant Yeast Isoleucyl–tRNA Synthetase," *The Journal of Biological Chemistry*, 266(26):17158–17164 (1991).

Walter, R.D. and Kuhlow, F., "Parasite–Specific Interaction of N–[4–(4' Nitroanilino)–Phenyl]–S–(β–Carboxyethyl)–Dithiocarbamic Acid–Ester with Arginyl–tRNA–Synthetase from *Dirofiliaria immitis*," *Trop. Med. Parasit.*, 36:230–232 (1985).

Chalker, A.F. et al., "Analysis and Toxic Overexpression in *Escherichia coli* of a Staphylococcal Gene Encoding Isoleucyl–tRNA Synthetase," *Gene*, 141:103–108 (1994).

Hughes, J. and Mellows, G., "Interaction of Pseudomonic Acid A with *Escherichia coli* B Isoleucyl–tRNA Synthetase," *Biochem J.*, 191:209–219 (1980).

von der Haar, F. et al., "Target Directed Drug Synthesis: The Aminoacyl–tRNA Synthetases as Possible Targets," *Angew. Chem. Int. Ed.*, 203(3):217–223 (1981).

Weygand–Duraševič, I. et al., "Yeast Seryl–tRNA Synthetase Expressed in *Escherichia coli* Recognizes Bacterial Serine–Specific tRNAs in vivo," *Eur. J. Biochem.*, 214:869–877 (1993).

Schlesinger, S. and Nester, E. W., "Mutants of *Escherichia coli* with an Altered Tyrosyl–Transfer Ribonucleic Acid Synthetase," *Journal of Bacteriology*, 100(1):167–175 (1969).

Meinnel, T. et al., "Aminoacyl–tRNA Synthetases: Occurrence, Structure, and Function." In *tRNA: Structure, Biosynthesis, and Function*, Söll, D. and RajBhandary, U., eds. (Washington, DC: American Society for Microbiology), pp. 251–300 (1995).

Orlova, V.S. et al., "Effect of Aerobic and Anaerobic Conditions on Chemical Composition and Enzyme Activity of Buds and Mother Cells of *Candida utilis*," *Prikladnaya Biokhimiya i Mikrobiologiya*, 13(2):260–264 (1977).

(List continued on next page.)

*Primary Examiner*—Robert A. Wax
*Assistant Examiner*—Lisa J. Hobbs
*Attorney, Agent, or Firm*—Hamilton, Brook, Smith & Reynolds, P.C.

[57] ABSTRACT

The present invention relates to isolated and/or recombinant nucleic acids which encode Candida tyrosyl-tRNA synthetases, portions thereof, or fusion proteins comprising a Candida tyrosyl-tRNA synthetase or portion thereof. Also disclosed are constructs comprising the nucleic acids of the present invention, host cells comprising a recombinant nucleic acid or construct, and methods of producing a Candida tyrosyl-tRNA synthetase, portion thereof, or fusion protein comprising same. Also described are tester strains, which are cells engineered to rely on the function of a Candida tyrosyl-tRNA synthetase or functional fragment thereof encoded by an introduced cloned gene, and which can be used in a method of detecting an inhibitor of Candida tyrosyl-tRNA synthetase function.

The invention further relates to isolated and/or recombinant Candida tyrosyl-tRNA synthetases, portions thereof, or fusion proteins comprising a Candida tyrosyl-tRNA synthetase or portion thereof, methods of use of these polypeptides in an assay to identify inhibitors of Candida tyrosyl-tRNA synthetase function, and antibodies reactive with Candida tyrosyl-tRNA synthetases.

38 Claims, 5 Drawing Sheets

OTHER PUBLICATIONS

Jasin, M. and Schimmel, P., "Deletion of an Essential Gene in *Escherichia coli* by Site–Specific Recombination with Linear DNA Fragments," *J. Bacteriol.,* 159(2):783–786 (1984).

Edwards, H. and Schimmel, P., "A Bacterial Amber Suppressor in *Saccharomyces cerevisiae* Is Selectively Recognized by a Bacterial Aminoacyl–tRNA Synthetase," *Molecular and Cellular Biology,* 10(4):1633–1641 (1990).

Shiba, K. et al., "Isolation of Higher Eukaryote Aminoacyl–tRNA Synthetase Genes by an Alignment–Guided Cross–Species PCR: Application to Human Isoleucine tRNA Synthetase," [From *Programme and Abstracts,* p. F.46], 15th International tRNA Workshop, Société Francaise de Biochimie et Biologie Moléculaire, Cap d'Agde, France, May 30–Jun. 4 (1993), Abstract No. 364.

Henkin, T. M. et al., "Analysis of the *Bacillus subtilis tyrS* Gene: Conservation of a Regulatory Sequence in Multiple tRNA Synthetase Genes," *Journal of Bacteriology,* 174(4):1299–1306 (1992).

Akins, R. A. and Lambowitz, A. M., "A Protein Required for Splicing Group I Introns in *Neurospora Mitochondria* Is Mitochondrial Tyrosyl–tRNA Synthetase or a Derivative Thereof," *Cell,* 50:331–345 (1987).

Hughes, J. et al., "Inhibition of Isoleucyl–Transfer Ribonucleic Acid Synthetase in *Escherichia coli* by Pseudomonic Acid," *Biochem. J.,* 176:305–318 (1978), Great Britain.

Kim, Sunghoon et al., "Diversified Sequences of Peptide Epitope for Same–RNA Recognition," *Proc. Natl. Acad. Sci. USA,* 90:10046–10050 (1993).

Shiba, K. and Schimmel, P., "Functional Asssembly of a Randomly Cleaved Protein," *Proc. Natl. Acad. Sci USA,* 89:1880–1884 (1992).

Shepard, A. et al., "RNA Binding Determinant in Some Class I tRNA Synthetases Identified by Alignment–Guided Mutagenesis," *Proc. Natl. Acad. Sci USA,* 89:9964–9968 (1992).

Ohyama, Takashi et al., "Studies on *T. utilis* tRNA$^{Tyr}$ Variants with Enzymatically Altered D–Loop Sequences. I. Deletion of the Conserved Sequence Gm–G and Its Effects on Aminoacylation and Conformation," *J. Biochem.,* 97:29–36 (1985).

Capobianco, John O. et al., "Anti–Candida Activity of Cispentacin: The Active Transport by Amino Acid Permeases and Possible Mechanisms of Action," *Biochemical and Biophysical Research Communications,* 190(3):1037–1044 (1993).

Houman, Fariba, et al., "Cloning Expression and Characterization of Isoleucyl Synthetase From *Candida albicans,*" Poster presented at Gordon Research Conference on Cellular and Molecular Mycology Holderness School, Plymouth, New Hampshire (Jun. 16–17, 1996).

Ohama, Takeshi, et al., "Non–Universal Decoding of the Leucine Codon CUG in Several Candida Species," *Nucleic Acids Research* 21(17):4039–4045 (1993).

Quinn, Cheryl L., et al., "Species–Specific Microhelix Aminoacylation by a Eukaryotic Pathogen tRNA Synthetase Dependent on a Single Base Pair," *Biochemistry,* 34(39):12489–12495 (1995).

Grundy, Frank J. and Henkin, Tina M., "Cloning and Analysis of the *Bacillus subtilis rpsD* Gene, Encoding Ribosomal Protein S4," *Journal of Bacteriology,* 172(11):6372–6379 (1990).

Winter, Greg et al., "The Amino Acid Sequence of the Tyrosyl–tRNA Synthetase from *Bacillus stearothermophilus,*" *Eur. J. Biochem.,* 133:383–387 (1983).

Glaser, P., et al., "A Gene Encoding a Tyrosine tRNA Synthetase Is Located Near sacS in *Bacillus subtilis,*" *J. DNA Sequencing and Mapping,* 1:251–261 (1991).

De Pouplana, L.R. et al., "Evidence That Two Present–Day Components Needed for the Genetic Code Appeared After Nucleated Cells Separated From Eubacteria," *Proc. Natl. Acad. Sci. USA,* 93:166–170 (1996).

Hashimoto, Shuichi, et al., "Nucleotide Sequence of Tyrosine Transfer RNA from *Torulopsis utilis,*" *The Journal of Biochemistry* 65(4):659–661 (1969).

Kaufman, C., "Cloning, Expression and Characterization of the Isoleucyl–tRNA Synthetase of *Candida albicans,*" Thesis, Naturwissenschaftliche Fakultät, Universität Witten/Herdecke, 1995.

Partial DNA sequence of *Candida albicans* gene now identified as MSY1 encoding mitochondrial tyrosyl–tRNA synthetase. *Candida albicans* information page: http://alces.med.umn.edu/candida/ourseqs/2031R.Seq; (Nov. 13, 1995).

5,871,987

CANDIDA TYROSYL-TRNA SYNTHETASE PROTEINS, NUCLEIC ACIDS AND STRAINS COMPRISING SAME

BACKGROUND OF THE INVENTION

*Candida albicans* is an opportunistic pathogen and the most common fungus causing systemic infections in man including both bloodstream infections in hospital immunocompromised patients and vaginal infections (for review, see: Mandell, G. L.; Bennett, J. E.; and Dolin, R. (Eds), Principles and Practice of Infectious Disease, 4th ed., Churchill Livingston: New York, 1995; Vol 2, Chapter 237). The increasing use of immunosuppressive therapy for malignancy and transplantation, the increase of intensive care patients receiving broad spectrum antibiotic therapy, and the AIDS epidemic have greatly increased the number of patients susceptible to opportunistic infections caused by *C. albicans*. In particular, infections due to Candida increased by almost 500% over the decade of the 1980's and continue to rise in the 1990's, becoming the fourth most common blood-stream pathogen (see: Pfaller, M. A. *Journal of Hospital Infection* 30 suppl:329–38 (1995)). It has been reported that 90% of AIDS patients have some type of Candida infection. *C. albicans* can invade the kidneys, heart, liver, lungs, spleen, brain and eyes. These infections are difficult to detect and can lead to death.

A limited number of antifungal agents are available for the treatment for *C. albicans* infections. Amphotericin B, the mainstay of antifungal therapy, has limited clinical utility in treating Candida infection due to its associated toxicities and requirement for intravenous administration. Flucytosine too is limited due to its bone marrow toxicity and to the appearance of resistance. The azole antifungal agents have become the first choice of therapy for Candida infections, and fluconazole is the most frequent drug prescribed in the 1990's. However, reports of resistance to these azole antifungals have appeared in recent years (see: Dupont, B. Current *Opinion in Infectious Diseases* 8:424–427 (1995)). Because of the development of resistance to antifungals and adverse side-effects of current therapies for Candida infection, there is continuing need for new drug targets and new antibiotics.

SUMMARY OF THE INVENTION

The invention relates to isolated and/or recombinant nucleic acids which encode tyrosyl-tRNA synthetases of Candida origin. The invention also relates to recombinant DNA constructs and vectors containing DNA having a sequence which encodes a tyrosyl-tRNA synthetase (TyrRS) of Candida origin or portions of the enzyme. These nucleic acids and constructs can be used to produce recombinant tyrosyl-tRNA synthetases of Candida origin.

A further embodiment of the invention is antisense nucleic acid which can hybridize to the nucleic acid which encodes a tyrosyl-tRNA synthetase of Candida. In cells, antisense nucleic acid can inhibit the function of an RNA which encodes a tyrosyl-tRNA synthetase of Candida.

The invention also relates to proteins or polypeptides, including fusion proteins, referred to herein as isolated and/or recombinant Candida tyrosyl-tRNA synthetases. These proteins are useful in the synthesis of peptides and related products, in assays to identify inhibitors of tyrosyl-tRNA synthetase function (including inhibitors having antimicrobial activity), in biochemical separations of tyrosine, and in quantitations of tyrosine and ATP. Antibodies which bind to tyrosyl-tRNA synthetases can be made and can be used in the purification and study of the enzyme.

Recombinant Candida tyrosyl-tRNA synthetases can be produced in host cells using cells and methods described herein. Tester strains, which are cells engineered to rely on the function of the tRNA synthetase encoded by an introduced cloned gene, are also an embodiment of the invention. Tester strains can be used to test the effectiveness and/or specificity of drug candidates in the inhibition of the essential tRNA synthetase enzyme encoded by the introduced cloned gene. In this way, potential inhibitors of the enzyme can be screened for antimicrobial or antibiotic effects, without requiring the culture of pathogenic strains of Candida, such as *Candida albicans*.

BRIEF DESCRIPTION OF THE DRAWINGS

FIG. 4A shows the expression and purification of an N-terminal GST-fusion protein of *C. albicans* tyrosyl-tRNA synthetase (TyrRS). Lanes 1 and 2: total soluble proteins from crude extracts of the GST-TyrRS fusion expression strain BL21(pC$^3$695). Lane 3: molecular weight markers. Lanes 4 and 5: GST-TyrRS fusion protein of *Candida albicans* after affinity purification as in Example 7A. (GST is glutathione S-transferase of *Schistosoma japonicum*.)

FIG. 4B shows the cleavage of the GST-moiety from the purified GST-TyrRS fusion protein from BL21(pC$^3$695). Lane 1: molecular weight markers. Lane 2: GST-TyrRS fusion protein following overnight incubation at 16° C. without the addition of thrombin. Lane 3: GST-TyrRS fusion protein following overnight incubation at 16° C. in the presence of 0.5 units of thrombin.

FIG. 6 is a graph illustrating the aminoacylation activity (cpm, counts per minute of [$^3$H]tyrosyl-tRNA) over time (minutes) of the purified N-terminal GST-TyrRS (28 nM) expressed from plasmid pC$^3$695, using crude total tRNA from brewer's yeast, for enzyme diluted 1:40,000 to 0.64 nM (■); 1:80,000 to 0.32 nM (♦); 1:160,000 to 0.16nM (▲); or no enzyme (○). Example 7B.)

Figure 1:
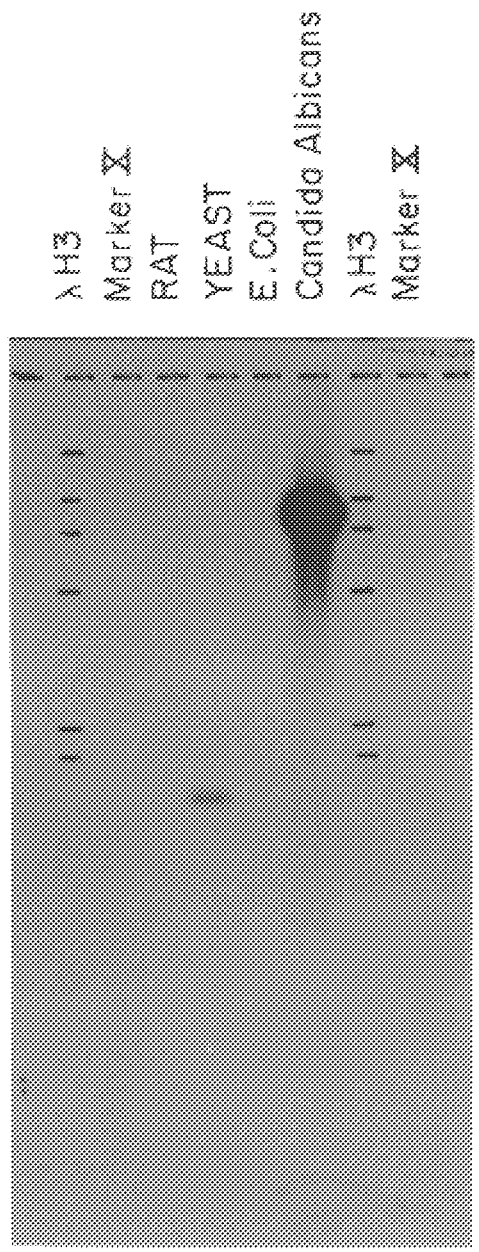
FIG. 1 is an illustration of a partial sequence (in IUPAC code; SEQ ID NO:40) of a 420 bp DNA fragment of the *C. albicans* mitochondrial tyrosyl-tRNA synthetase gene, isolated by PCR (see Examples 1 and 2). The amino acid translation for the predicted open reading frame is also shown (SEQ ID NO:41; "?"=Xaa).

FIG. 7 is a graph showing aminoacylation activity (cpm, counts per minute of [$^3$H]tyrosyl-tRNA) over time (minutes) of *C. albicans* tyrosyl-tRNA synthetase partially purified as in Example 8, using crude total tRNA from brewer's yeast as substrate.

DETAILED DESCRIPTION OF THE INVENTION

The aminoacyl-tRNA synthetases are enzymes with the common general function of catalyzing the following reaction:

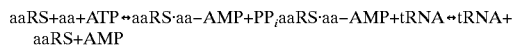

(aaRS=aminoacyl-tRNA synthetase; aa=amino acid; ATP=adenosine 5-triphospate; AMP=adenosine 5'-monophosphate; $PP_i$=inorganic pyrophosphate) The second (aminoacylation) step is often referred to as "charging" the tRNA.

Generally, in each bacterial organism, there are 20 aminoacyl-tRNA synthetases, each specific for a different amino acid. Eucaryotic organisms also typically encode 20 cytoplasmic aaRSs, one specific for each amino acid. In addition, eucaryotic organisms generally encode a separate set of mitochondrial aaRSs. In the yeast *Saccharomyces cerevisiae*, the cytoplasmic and mitochondrial enzymes are usually encoded by separate nuclear genes, however exceptions have been found in which one gene encodes both cytoplasmic and mytochondrial enzyme (Natsoulis, G., et al., *Cell* 46:235–243 (1986); Chatton, B., et al., *J. Biol. Chem.* 263:52–57 (1988)). Each aminoacyl-tRNA synthetase enzyme recognizes and reacts with a specific amino acid and with one or more tRNAs that recognize the codons specific for that amino acid (cognate tRNAs). The specificity of the aaRS for the amino acid is determined by protein-amino acid interactions, and the specificity of the aaRS for the tRNA is determined by protein-RNA interactions, using different sites on the aaRS and tRNA molecules.

The tRNA synthetases can be subdivided into two groups of enzymes, class I and class II, based on short regions of sequence homology as well as distinct active site core tertiary structures (Eriani, G., et al., *Nature* 347:203–206 (1990); Moras, D., *Trends Biochem. Sci.* 17:159–164 (1992); Burbaum, J. J. and Schimmel, P., *J. Biol Chem.* 266(26): 16965–16968 (1991)). Tyrosyl-tRNA synthetase has been classified as a class I synthetase. This enzyme contains the signature peptide sequences, HIGH and KMSKS, corresponding to motifs that are part of the nucleotide binding fold present in all class I synthetases.

Nucleic Acids, Constructs and Vectors

The present invention relates to isolated and/or recombinant (including, e.g., essentially pure) nucleic acids having sequences which encode a Candida tyrosyl-tRNA synthetase, or a portion of a Candida tyrosyl-tRNA synthetase. In one embodiment, the nucleic acid or portion thereof encodes a protein or polypeptide having at least one function characteristic of a Candida tyrosyl-tRNA synthetase, such as a catalytic activity (e.g., catalysis of tyrosyl-adenylate formation, catalysis of aminoacylation of a tRNA with tyrosine), and/or binding function (e.g., tRNA-, tyrosine- or ATP-binding), and/or antigenic function (e.g., binding of antibodies that also bind to naturally occurring Candida TyrRS), and/or oligomerization function. Oligomerization activity is the ability of a protein subunit or protein fragment to bind together with one or more other protein subunits or protein fragments, thus altering the quaternary structure of the resulting complex. For example, "adhesive" fragments with oligomerization activity can bind to another fragment with no catalytic activity of its own to restore or partially restore enzymatic activity (Jasin, M., et al., U.S. Pat. No. 4,952,501). The present invention also relates more specifically to isolated and/or recombinant nucleic acids or a portion thereof having sequences which encode a tyrosyl-tRNA synthetase of *Candida albicans* origin, or a portion thereof.

Figure 3:
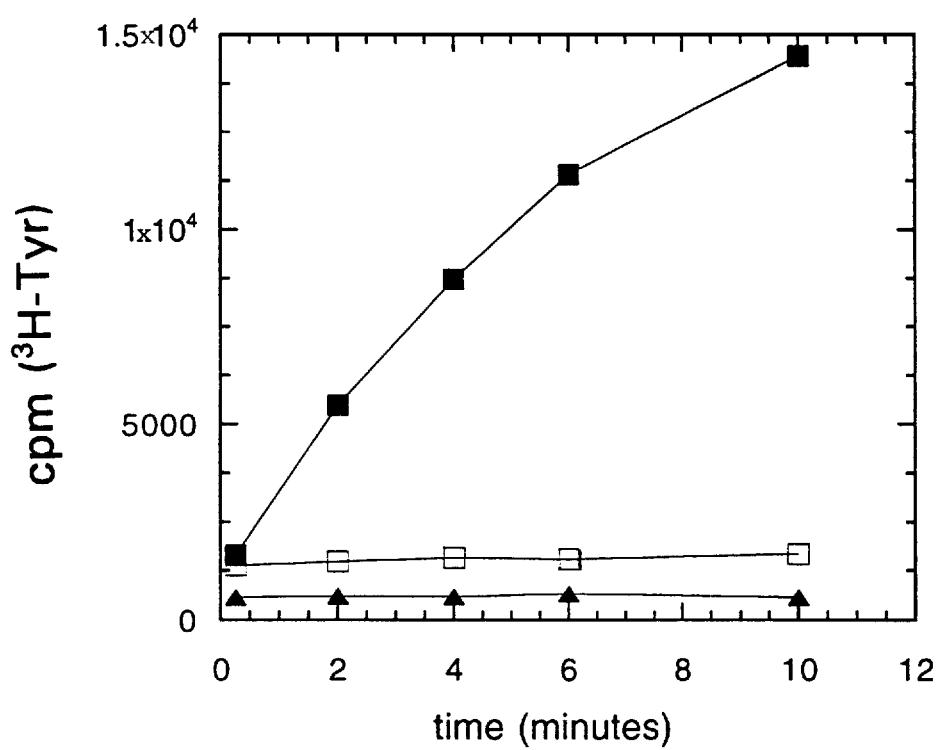
FIGS. 3A–3B are an illustration of the 1430 basepair nucleotide sequence determined for the tyrosyl-tRNA synthetase gene of *C. albicans* (ORF and flanking sequences, SEQ ID NO:1), and the amino acid sequence of the protein as translated by the universal genetic code, starting from the initiator methionine codon at base 134 (SEQ ID NO:2). Standard single letter amino acid codes are used.

The invention further relates to isolated and/or recombinant nucleic acids that are characterized by (1) their ability to hybridize to a nucleic acid having the sequence of FIGS. 3A–3B (SEQ ID NO:1) or of FIG. 1 (SEQ ID NO:40), or portions of either of the foregoing (e.g., a portion comprising the open reading frame); or (2) by their ability to encode a polypeptide having the amino acid sequence of a Candida tyrosyl-tRNA synthetase (e.g., SEQ ID NO:39), a portion thereof or functional equivalents thereof (e.g., a polypeptide which aminoacylates the isoaccepting cognate tRNAs (such as tRNA$^{Tyr}$ of *C. albicans*) with tyrosine); or (3) by both characteristics. A nucleic acid which hybridizes to a nucleic acid encoding a Candida TyrRS such as SEQ ID NO:1, can be double- or single-stranded. Hybridization to DNA such as DNA having the sequence SEQ ID NO:1 includes hybridization to the strand shown or its complementary strand. In one embodiment, the percent amino acid sequence similarity between a Candida tyrosyl-tRNA synthetase, such as the polypeptide encoded by SEQ ID NO:1 and functional equivalents thereof is at least about 80% ($\geq$80%). In a preferred embodiment, the percent amino acid sequence similarity between between a Candida tyrosyl-tRNA synthetase and its functional equivalents is at least about 85% ($\geq$85%). More preferably, the percent amino acid sequence similarity between between a Candida tyrosyl-tRNA synthetase and its functional equivalents is at least about 90%, and still more preferably, at least about 95%.

Isolated and/or recombinant nucleic acids meeting these criteria comprise nucleic acids having sequences identical to sequences of naturally occurring Candida TyrRS genes, including allelic variants, and portions thereof, or variants of the naturally occurring sequences. Such variants include mutants differing by the addition, deletion or substitution of one or more residues, modified nucleic acids in which one or more residues are modified (e.g., DNA or RNA analogs), and mutants comprising one or more modified residues. Preferred embodiments of isolated and/or recombinant nucleic acids are those encoding tyrosyl-tRNA synthetases of Candida species other than *C. utilis*; particularly preferred are isolated and/or recombinant nucleic acids encoding tyrosyl-tRNA synthetases of pathogenic species, including, but not limited to, *C. albicans, C. pseudotropicalis, C. stellatoidea, C. guilliermondi, C. glabrata, C. krusei, C. parapsilosis,* and *C. tropicalis*.

Such nucleic acids, including DNA or RNA, can be detected and isolated by hybridization under high stringency conditions or moderate stringency conditions, for example. "Stringency conditions" for hybridization is a term of art which refers to the conditions of temperature and buffer concentration which permit hybridization of a particular nucleic acid to another nucleic acid in which the first nucleic acid may be perfectly complementary to the second, or the first and second may share only some degree of complementarity. For example, certain high stringency conditions can be used which distinguish perfectly complementary nucleic acids from those of less complementarity. "High stringency conditions" and "moderate stringency conditions" for nucleic acid hybridizations are explained on pages 2.10.1–2.10.16 (see particularly 2.10.8–11) and pages 6.3.1–6 in *Current Protocols in Molecular Biology* (Ausubel, F. M., et al., Eds., Vol. 1, containing supplements up through Supplement 29, 1995), the teachings of which are hereby incorporated by reference. The exact conditions which determine the stringency of hybridization depend not only on ionic strength, temperature and the concentration of destabilizing agents such as formamide, but also on factors such as the length of the nucleic acid sequence, base composition, percent mismatch between hybridizing sequences and the frequency of occurrence of subsets of that sequence within other non-identical sequences. Thus high or moderate stringency conditions can be determined empirically.

For example, if a set of hybridization conditions is used which is determined to allow hybridization between nucleic acids which are too dissimilar in sequence for the purposes of an experiment, then the hybridization conditions can be altered in subsequent experiments to a higher stringency to achieve selectivity to the desired level of sequence similarity. Higher stringency conditions can be achieved, for example, by raising the temperature of the hybridization and post-hybridization washes, and/or by decreasing the ionic strength (usually, the SSC concentration) of the hybridization buffer and post-hybridization washes. This strategy can be applied, for example, to exclude cross-hybridization of a *C. albicans* probe to *S. cerevisiae* DNA which may occur. For example, starting from the "high stringency" conditions given in Example 3A, stringency can be increased to "very high stringency" conditions under which hybridization to *S. cerevisiae* DNA does not occur.

By varying hybridization conditions from a level of stringency at which no hybridization occurs to a level at which hybridization is first observed, conditions which will allow a given sequence to hybridize with the most similar sequences in the sample can also be determined.

Exemplary conditions are described in Krause, M. H. and Aaronson, A. S.; *Methods in Enzymology*, 200:546–556 (1991). Also see especially page 2.10.11 in *Current protocols in Molecular Biology (supra)*, which describes how to determine washing conditions. Washing is the step in which conditions are usually set so as to determine a minimum level of complementarity of the hybrids and eliminate free non-hybridized radioactive probe as well as background and non-specific weak interaction. Generally, starting from the lowest temperature at which only homologous hybridization occurs, each degree Celsius by which the final wash temperature is reduced (holding SSC concentration constant) allows an increase by 1% in the maximum extent of mismatching among the sequences that hybridize. Generally, doubling the concentration of SSC results in an increase in $T_m$ of ~170 C. Using these guidelines, the washing temperature can be determined empirically for high, moderate or low stringency, depending on the level of mismatch sought.

Isolated and/or recombinant nucleic acids that are characterized by their ability to hybridize to a nucleic acid encoding a Candida tyrosyl-tRNA synthetase such as the nucleic acid depicted in SEQ ID NO:1, or a portion thereof (e.g. under high or moderate stringency conditions), may further encode a protein or polypeptide having at least one function characteristic of a Candida tyrosyl-tRNA synthetase, such as a catalytic activity (e.g., tyrosyl-adenylate formation, aminoacylation of a tRNA with tyrosine), binding function (e.g., tRNA-, tyrosine-, or ATP-binding), antigenic function (e.g., binding of antibodies that also bind to non-recombinant Candida TyrRS), and/or oligomerization function. The catalytic or binding function of a protein or polypeptide encoded by hybridizing nucleic acid may be detected by standard enzymatic assays for activity or binding (e.g., assays which monitor aminoacyl-adenylate formation, aminoacylation of tRNA with tyrosine). Functions characteristic of a tyrosyl-tRNA synthetase may also be assessed by in vivo complementation activity or other suitable methods. Enzymatic assays, complementation tests, or other suitable methods can also be used in procedures for the identification and/or isolation of nucleic acids which encode a polypeptide such as a polypeptide of the amino acid sequence SEQ ID NO:2, or functional equivalents of these polypeptides. The antigenic properties of proteins or polypeptides encoded by hybridizing nucleic acids can be determined by immunological methods employing antibodies that bind to a Candida tyrosyl-tRNA synthetase, such as immunoblot, immunoprecipitation and radioimmunoassay.

The identification of nucleic acids with sequences related to those of the *C. albicans* TyrRS gene is not limited to hybridization methods. The identification of additional Candida TyrRS genes can also be accomplished by an extension of the methods used to isolate *Candida albicans* TyrRS-specific fragments as explained in Examples 1–3. For example, pairs of degenerate oligonucleotides that were successfully used in a PCR reaction to identify the *C. albicans* cytoplasmic TyrRS gene and TyrRS mitochondrial fragment can be used in PCR reactions using the reaction conditions described below or other suitable conditions. Since these primer pairs, which were created based upon DNA sequence information of non-Candida species, were able to amplify a *C. albicans* PCR product, it is reasonable to expect that they can amplify a PCR product from other related Candida species. The same degenerate primer pairs that were used in PCR reactions to isolate *C. albicans* TyrRS-specific fragments can be used with a suitable template from other Candida species, (e.g., genomic DNA, a cloned library). Once a fragment of the Candida species TyrRS is generated by PCR, it can be sequenced. To determine if the DNA sequence of the PCR product encodes a TyrRS, the sequence of the product can be compared to other DNA sequences. The entire gene sequence (including the 5' and 3' ends) can then be identified. For example, semi-specific PCR can be used.

A tyrosyl-tRNA synthetase gene or portion thereof is producible by methods described herein or other suitable methods. For example, primers (e.g., a pair of primers or nested primers) can be designed which comprise a sequence which is complementary or substantially complementary to a portion of the gene encoding *C. albicans* TyrRS. Primers can contain portions which are complementary to other sequences as appropriate, such as restriction recognition sequences, template sequences (e.g., vector sequences flanking the inserts in a gene library) or other sequences. For instance, primers complementary to the 5'- and 3' ends of the coding sequence and or flanking regions shown in FIGS. 3A–3B (SEQ ID NO:1) can be designed. Such primers can be used in a polymerase chain reaction with a suitable nucleic acid template (e.g., a construct described herein, a library or another suitable nucleic acid) to obtain a *C. albicans* TyrRS gene or portion thereof.

Nucleic acids of the present invention can be used in the production of proteins or polypeptides. For example, DNA containing all or part of the coding sequence for a Candida tyrosyl-tRNA synthetase, or DNA which hybridizes to DNA having the sequence SEQ ID NO:1, can be incorporated into various constructs and vectors created for further manipulation of sequences or for production of the encoded polypeptide in suitable host cells.

Nucleic acids referred to herein as "isolated" are nucleic acids separated away from the nucleic acids of the genomic DNA or cellular RNA of their source of origin (e.g. as it exists in cells or in a mixture of nucleic acids such as a library), and may have undergone further processing. Isolated nucleic acids include nucleic obtained by methods described herein, similar methods or other suitable methods, including essentially pure nucleic acids, nucleic acids produced by chemical synthesis, by combinations of biological and chemical methods, and recombinant nucleic acids which are isolated. Nucleic acids referred to herein as "recombinant" are nucleic acids which have been produced by recombinant DNA methodology, including those nucleic acids that are generated by procedures which rely upon a method of artificial recombination, such as the polymerase chain reaction (PCR) and/or cloning into a vector using restriction enzymes. "Recombinant" nucleic acids are also those that result from recombination events that occur through the natural mechanisms of cells, but are selected for after the introduction into the cells of nucleic acids designed to allow and make probable a desired recombination event.

Portions of the isolated nucleic acids which code for polypeptides having a certain function can be identified and isolated by, for example, the method of Jasin, M., et al., U.S. Pat. No. 4,952,501.

A further embodiment of the invention is antisense nucleic acid, which is complementary, in whole or in part, to a target molecule comprising a sense strand, and can hybridize with the target molecule. The target can be DNA, or its RNA counterpart (i.e., wherein T residues of the DNA are U residues in the RNA counterpart). When introduced into a cell, antisense nucleic acid can inhibit the expression of the gene encoded by the sense strand. Antisense nucleic acids can be produced by standard techniques.

In a particular embodiment, the antisense nucleic acid is wholly or partially complementary to and can hybridize with a target nucleic acid, wherein the target nucleic acid can hybridize to a nucleic acid having the sequence of the complement of the top strand shown in FIGS. 3A–3B (SEQ ID NO:1). For example, antisense nucleic acid can be complementary to a target nucleic acid having the sequence shown as the top strand of the open reading frame in FIGS. 3A–3B (SEQ ID NO:1), or to a portion thereof sufficient to allow hybridization. In another embodiment, the antisense nucleic acid is wholly or partially complementary to and can hybridize with a target nucleic acid which encodes a Candida tyrosyl-tRNA synthetase.

*C. albicans* is the most important human pathogen among Candida species. Because advances in the understanding and treatment of *C. albicans* infection would be of benefit, it was the species selected for most of the experimental work described herein. As described in the Exemplification, PCR fragments of *C. albicans* TyrRS genes were isolated, cloned and used as probes to screen two genomic libraries of *C. albicans* (Goshorn, A., et al., *Infect. Immun.* 60:876–884 (1992), Goshorn, A. and Scherer, S. *Genetics* 123:667–673 (1989), Kwon-Chung, K. J. et al., *Infect. Immun.* 49:571–575 (1985), Slutsky, B. M., et al., *J. Bacteriol.*169:189 (1987); Baldari, C. and Cesareni, G., *Gene* 35:27, (1985)).

The isolated *C. albicans* gene is representative of a broader class of Candida tyrosyl-tRNA synthetase genes derived from various species of Candida. These additional genes can also be used to express Candida tyrosyl-tRNA synthetases, with utilities corresponding to those described herein, and can be used in the production of host cells and tester strains comprising recombinant Candida tyrosyl-tRNA synthetase genes using methods described herein. The approaches described herein, including, but not limited to, the approaches to isolate and manipulate the tyrosyl-tRNA synthetase gene of *C. albicans*, to construct vectors and host strains, and to produce and use the protein, to produce antibodies, etc., can be applied to other members of the genus Candida, including, but not limited to, pathogenic species such as *C. pseudotropicalis, C. stellatoidea, C. guilliermondi, C. glabrata, C. krusei, C. parapsilosis,* and *C. tropicalis*. For example, the tyrosyl-tRNA synthetase gene described here or sufficient portion thereof, whether isolated and/or recombinant or synthetic, including fragments produced by PCR, can be used to detect and/or recover homologous genes of the other Candida species (e.g., as probes for hybridization, or primers for PCR or other suitable techniques).

Proteins

It should be noted that certain species of Candida, including *C. albicans, C. parapsilosis, C. zeylanoldes, C. rugosa, C. melibiosica* and *C. cylindracea*, are known to use a variation of the "universal" genetic code which appears in genetics textbooks and treatises (for example, see pages 104–105 in Lewin, B., *Genes,* 3rd edition, John Wiley and Sons, New York, 1987; Ohama, T. et al., *Nucleic Acids Res.* 21:4039–4045 (1993)). It is known that in these species of Candida, the codon CUG, which codes for leucine in the universal genetic code, is decoded as serine by a non-universal genetic code of these species of Candida. It is possible that in these species of Candida, other codons may also determine a different amino acid from that determined by the universal code. Thus, the expression of a gene, such as a TyrRS gene, in certain species of Candida, can result in a protein having a different amino acid sequence from the amino acid sequence that would result from the expression of the same gene in an organism using the universal genetic code. Other species of Candida decode CUG as leucine, including *C. magnoliae, C. azyma, C. diversa,* and *C. rugopelliculosa* (Ohama et al.).

The invention relates further to proteins or polypeptides encoded by nucleic acids of the present invention. The proteins and polypeptides of the present invention can be isolated and/or recombinant. Proteins or polypeptides referred to herein as "recombinant" are proteins or polypeptides produced by the expression of recombinant nucleic acids. Proteins or polypeptides referred to herein as "isolated" are proteins or polypeptides purified to a state beyond that in which they exist in cells, and include proteins or polypeptides obtained by methods described herein, similar methods or other suitable methods, including essentially pure proteins or polypeptides, proteins or polypeptides produced by chemical synthesis, or by combinations of biological and chemical methods, and recombinant proteins or polypeptides which are isolated. Preferred embodiments of isolated and/or recombinant proteins are tyrosyl-tRNA synthetases of Candida other than *C. utilis*; particularly preferred are isolated and/or recombinant tyrosyl-tRNA synthetases of pathogenic species, including, but not limited to, *C. albicans, C. pseudotropicalis, C. stellatoidea, C. guilliermondi, C. glabrata, C. krusei, C. parapsilosis,* and *C. tropicalis*.

In one embodiment, proteins or polypeptides are isolated to a state at least about 65 pure; more preferably at least about 75% pure, and still more preferably at least about 85% pure, as determined by Coomassie blue staining of proteins on SDS-polyacrylamide gels.

In a preferred embodiment, the protein or portion thereof has at least one function characteristic of a Candida tyrosyl-tRNA synthetase, for example, catalytic activity (e.g., catalysis of aminoacyl-adenylate formation, catalysis of aminoacylation of tRNA with tyrosine), binding function (e.g., tRNA-, amino acid-, or ATP-binding), antigenic function (e.g., binding of antibodies that also bind to non-recombinant Candida tyrosyl-tRNA synthetase), and/or oligomerization activity. As such, these proteins are referred to as tyrosyl-tRNA synthetases of Candida origin or Candida tyrosyl-tRNA synthetases, and include, for example, naturally occurring Candida tyrosyl-tRNA synthetases (including allelic variants), variants (e.g. mutants) of those proteins and/or portions thereof. Such variants include mutants differing by the addition, deletion or substitution of one or more amino acid residues, or modified polypeptides in which one or more residues are modified, and mutants comprising one or more modified residues.

In a particularly preferred embodiment, like naturally occurring Candida tyrosyl-tRNA synthetase, isolated and/or recombinant Candida tyrosyl-tRNA synthetases of the present invention aminoacylate the isoaccepting cognate tRNAs of the Candida organism with tyrosine in a two-step reaction. For example, an isolated, recombinant *C. albicans* tyrosyl-tRNA synthetase is able to aminoacylate each of the isoaccepting species of cognate tRNA$^{Tyr}$ of *C. albicans* with tyrosine. In the first step, the Candida tyrosyl-tRNA synthetase catalyzes the covalent linkage of tyrosine to ATP to form an adenylate complex (tyrosyl-adenylate) with the release of pyrophosphate, and, in a second step, catalyzes the covalent linkage of tyrosine to a specific tRNA recognized by the enzyme, releasing AMP.

The invention further relates to fusion proteins, comprising a Candida tyrosyl-tRNA synthetase (as described above) as a first moiety, linked to second moiety not occurring in the Candida TyrRS as found in nature. Thus, the second moiety can be an amino acid or polypeptide. The first moiety can be in an N-terminal location, C-terminal location or internal to the fusion protein. In one embodiment, the fusion protein comprises a *C. albicans* tyrosyl-tRNA synthetase as the first moiety, and a second moiety comprising a linker sequence and affinity ligand.

Fusion proteins can be produced by a variety of methods. For example, a fusion protein can be produced by the insertion of a TyrRS gene or portion thereof into a suitable expression vector, such as Bluescript SK ± (Stratagene), pGEX-4T-2 (Pharmacia) and pET-15b (Novagen). The resulting construct is then introduced into a suitable host cell for expression. Upon expression, fusion protein can be purified from a cell lysate by means of a suitable affinity matrix (see e.g., *Current Protocols in Molecular Biology* (Ausubel, F. M., et al., Eds., Vol. 2, Suppl. 26, pp. 16.4.1–16.7.8 (1991)).

The invention also relates to isolated and/or recombinant portions or fragments of a tyrosyl-tRNA synthetase of Candida origin. Portions of the enzyme can be made which have full or partial function on their own, or which when mixed together (though fully, partially, or nonfunctional alone), spontaneously assemble with one or more other polypeptides to reconstitute a functional protein having at least one function characteristic of a Candida tyrosyl-tRNA synthetase. (See, e.g., Shiba, K. and Schimmel, P., *J. Biol. Chem.* 267:22703–22706 (1992) for an example of three inactive peptides from *E. coli* IleRS spontaneously assembling in vivo to reconstitute active enzyme; see also, Burbaum, J. and Schimmel, P., *Biochemistry* 30(2): 319–324 (1991), describing non-overlapping segments of *E. coli*-MetRS that can fold together to reconstitute an active enzyme capable of recognizing and charging tRNA in vitro and in vivo; see also Jasin, M., et al., (U.S. Pat. No. 4,952,501) describing deletion studies of *E. coli* alanyl-tRNA synthetase which showed that large portions of the protein were unnecessary for specific aminoacylation activity). Based on this type of analysis, portions of a Candida TyrRS can be made which have at least one function characteristic of a Candida tyrosyl-tRNA synthetase, such as a catalytic function, binding function, antigenic function and/or oligomerization function. Studies on the structure and function of the aaRSs provide the basis for being able to divide the Candida aaRS enzymes into functional domains (Schimmel, P., *Current Biology* 1:811–816 (1991)).

The sequences and structures of the catalytic domains of several tRNA synthetases which have been purified and studied have led to the identification of two distinct classes designated class I and class II (Schimmel, P., *Ann. Rev. Biochem.* 56:125–158 (1987); Webster, T. A., et al., *Science* 226:1315–1317 (1984); Eriani, G., et al, *Nature* 347:203–206 (1990) and Cusack, S., et al., *Nature* 347:249–255 (1990)). Class I enzymes have a well-conserved N-terminal nucleotide binding fold responsible for amino acid binding, aminoacyl-adenylate formation, and tRNA acceptor helix docking. The N-terminal Rossman nucleotide binding fold is comprised of alternating β-strands and a-helices and comprises conserved motifs such as the HIGH tetrapeptide located in the first half of the Rossman fold and the KMSKS pentapeptide located in the second half of the Rossman fold. These elements are landmarks of class I synthetases. The C-terminal domain is rich in a-helices and contains residues needed for interactions with the parts of the tRNA distal to the amino acid attachment site (Shepard, A., et al., *Proc. Natl. Acad. Sci. U.S.A.* 89:9964–9968 (1992); Hou, Y.-M., et al., *Proc. Natl. Acad. Sci. U.S.A.* 88:976–980 (1991)). In some tRNA synthetases, this second domain interacts directly with the anticodon (Rould, M. A., et al., *Science* 246:1135–1142 (1989) and Cavarelli, J., et al., *Nature* 362:181–184 (1993)), while in other enzymes there is no contact made between the second domain and the anticodon (Biou, V., et al., *Science* 263:1404–1410 (1994)). To a first approximation, the two domains in class I tRNA synthetases interact with the two distinct domains of the L-shaped tRNA structure. Thus, the recognition elements of the tRNA synthetase and of the tRNA which are needed for the operational RNA code are segregated into discrete protein and RNA domains.

Consideration of this information, along with the remaining teachings of the specification, allows the construction of *C. albicans* tyrosyl-tRNA synthetase derivatives which possess at least one function characteristic of a Candida tyrosyl-tRNA synthetase.

Method of Producing Recombinant TyrRSs

Another aspect of the invention relates to a method of producing a Candida tyrosyl-tRNA synthetase or a portion thereof, and to expression systems and host cells containing a vector appropriate for expression of the Candida tyrosyl-tRNA synthetase.

Cells that express a recombinant tyrosyl-tRNA synthetase or a portion thereof can be made and maintained in culture under conditions suitable for expression to produce protein for isolation and purification. These cells can be procaryotic or eucaryotic. Examples of procaryotic cells that can be used to express Candida tyrosyl-tRNA synthetases include *Escherichia coli*, (e.g., BL21, BL22, JM109), *Bacillus subtilis* and other bacteria. Examples of eucaryotic cells that can be used to express the tyrosyl-tRNA synthetases include yeasts such as *Saccharomyces cerevisiae, S. pombe, Pichia pastoris*, and other lower eucaryotic cells, as well as cells of higher eucaryotes, such as those from insects and mammals. (See, e.g., Ausubel, F. M. et al., Eds. *Current Protocols in Molecular Biology*, Greene Publishing Associates and John Wiley & Sons Inc., (1993)).

In one embodiment, host cells that produce a recombinant Candida TyrRS protein or portion thereof for isolation and purification can be made as follows. A gene encoding a TyrRS can be inserted into a nucleic acid vector, e.g., a DNA vector, such as a plasmid, virus or other suitable replicon, which can be present in a single copy or multiple copies, or the gene can be integrated in a host cell chromosome. Such a suitable replicon contains all or part of the coding sequence for Candida tyrosyl-tRNA synthetase operably linked to one or more expression control sequences whereby the coding sequence is under the control of transcription signals and linked to appropriate translation signals to permit translation of the TyrRS, portion thereof, or of a fusion protein comprising an TyrRS or portion thereof. The vector can be introduced into cells by a method appropriate to the type of host cells (e.g., transformation, electroporation, transfection, infection). For expression from the TyrRS gene, the host cells can be maintained under appropriate conditions, e.g., in the presence of inducer, normal growth conditions, etc.).

For example, Candida tyrosyl-tRNA synthetase can be produced by integrating a gene encoding the *C. albicans* TyrRS into the genome of a virus that enters the host cells. By infection of the host cells, the components of a system which permits the transcription and translation of the Candida TyrRS gene are present in the host cells. Alternatively, an RNA polymerase gene, inducer, or other component required to complete such a gene expression system may be introduced into the host cells already containing the Candida TyrRS gene, for example, by means of a virus that enters the host cells and contains the required component. The Candida TyrRS gene can be under the control of an inducible or constitutive promoter. The promoter can be one that is recognized by the host cell RNA polymerase. The promoter can, alternatively, be one that is recognized by a viral RNA polymerase and is transcribed following infection of the host cells with a virus.

Antibodies

The invention further relates to antibodies that bind to an isolated and/or recombinant Candida tyrosyl-tRNA synthetase, including portions of antibodies (e.g., a peptide), which can specifically recognize and bind to the tyrosyl-tRNA synthetase. These antibodies can be used in methods to purify the enzyme or portion thereof, for example by immunoaffinity chromatography, or to selectively inactivate one of the enzyme's active sites, or to study other aspects of enzyme structure, for example.

The antibodies of the present invention can be polyclonal or monoclonal, and the term antibody is intended to encompass both polyclonal and monoclonal antibodies. Antibodies of the present invention can be raised against an appropriate immunogen, including proteins or polypeptides of the present invention, such as an isolated and/or recombinant Candida tyrosyl-tRNA synthetase or portion thereof, or synthetic molecules, such as synthetic peptides. The immunogen, for example, can be a protein having at least one function of a Candida tyrosyl-tRNA synthetase, as described herein.

The term antibody is also intended to encompass single chain antibodies, chimeric, humanized or primatized (CDR-grafted) antibodies, and the like, as well as chimeric or CDR-grafted single chain antibodies, comprising portions from more than one species. For example, the chimeric antibodies can comprise portions of proteins derived from two different species, joined together chemically by conventional techniques or prepared as a contiguous protein using genetic engineering techniques (e.g., DNA encoding the protein portions of the chimeric antibody can be expressed to produce a contiguous protein chain). See, e.g., Cabilly, et al., U.S. Pat. No. 4,816,567; Cabilly, et al., European Patent No. 0,125,023 B1; Boss, et al., U.S. Pat. No. 4,816,397; Boss, et al., European Patent No. 0,120,694 B1; Neuberger, M. S., et al., WO 86/01533; Neuberger, M. S., et al., European Patent No. 0,194,276 B1; Winter, U.S. Pat. No. 5,225,539; and Winter, European Pat. No. 0,239, 400 B11. See also, Newman, R., et al., *BioTechnology* 10: 1455–1460 (1992), regarding primatized antibody, and Ladner, et al., U.S. Pat. No. 4,946,778 and Bird, R. E., et al., *Science* 242: 423–426 (1988)) regarding single chain antibodies.

Whole antibodies and biologically functional fragments thereof are also encompassed by the term antibody. Biologically functional antibody fragments which can be used include those fragments sufficient for binding of the antibody fragment to a Candida TyrRS to occur, such as Fv, Fab, Fab' and $F(ab')_2$ fragments. Such fragments can be produced by enzymatic cleavage or by recombinant techniques. For instance, papain or pepsin cleavage can enerate Fab or $F(ab')_2$ fragments, respectively. Antibodies can also be produced in a variety of truncated forms using antibody genes in which one or more stop codons have been introduced upstream of the natural stop site. For example, a chimeric gene encoding a $F(ab')_2$ heavy chain portion can be designed to include DNA sequences encoding the $CH_1$ domain and hinge region of the heavy chain.

Preparation of immunizing antigen, and polyclonal and monoclonal antibody production can be performed using any suitable technique. A variety of methods have been described (see e.g., Kohler, et al., *Nature* 256: 495–497 (1975) and *Eur. J. Immunol.* 6: 511–519 (1976); Milstein, et al., *Nature* 266: 550–552 (1977); Koprowski, et al., U.S. Pat. No. 4,172,124; Harlow, E. and Lane, D.; 1988, *Antibodies: A Laboratory Manual*, (Cold Spring Harbor Laboratory: Cold Spring Harbor, N.Y.); *Current Protocols In Molecular Biology*, Vol. 2 (Supplement 27, Summer '94), Ausubel, F. M., et al., Eds., (John Wiley & Sons: New York, N.Y.), Chapter 11, (1991)). Generally, a hybridoma is produced by fusing a suitable immortal cell line (e.g., a myeloma cell line such as SP2/0) with antibody producing cells. The antibody producing cell, preferably those obtained from the spleen or lymph nodes, can be obtained from animals immunized with the antigen of interest. The fused cells (hybridomas) can be isolated using selective culture conditions, and cloned by limiting dilution. Cells which produce antibodies with the desired specificity can be selected by a suitable assay (e.g., ELISA).

Assays for Inhibitors and Tester Strains

The enzymatic assays, binding assays, and construction of tester strains described below, which rely upon the nucleic acids and proteins of the present invention, can be used, alone or in combination with each other or other suitable methods, to identify inhibitors of one or more Candida tyrosyl-tRNA synthetases.

Enzyme Assay

Upon isolation from a species of the genus Candida, a TyrRS gene can be incorporated into an expression system for production of the TyrRS enzyme as a native or a fusion protein, followed by isolation and testing of the enzyme in vitro. The isolated or purified Candida TyrRSs can also be used in further structural studies that allow for the design of antibiotics which specifically target one or more aaRSs of Candida, while not affecting or minimally affecting host or mammalian (e.g., human) aaRSs. Because the amino acid sequences of the tRNA synthetases have diverged over evolution, significant differences exist between the structure of the enzymes from mammals (e.g., human, bovine) and mammalian pathogens, and the design or selection of inhibitors can exploit the structural differences between the pathogen aaRS and the host (e.g., a mammalian host, such a human) aaRS to yield specific inhibitors of the pathogen aaRS, which may further have antimicrobial activity.

Furthermore, isolated, active Candida TyrRSs can be used in an in vitro method of screening for inhibitors of tyrosyl-tRNA synthetase activity in which the inhibitory effect of a compound is assessed by monitoring TyrRS activity according to standard techniques. For example, inhibitors of the activity of isolated, recombinant C. albicans TyrRS can be identified by the method. In one embodiment, the isolated TyrRS enzyme is maintained under conditions suitable for tyrosyl-adenylate formation, the enzyme is contacted with a compound to be tested, and formation of the tyrosyl-adenylate is monitored by standard assay. A reduction in the activity measured in the presence of compound, as compared with the activity in the absence of compound, is indicative of inhibition of tyrosyl-tRNA synthetase activity by the compound.

For example, the extent of tyrosyl-adenylate formation catalyzed by purified TyrRS can be measured using an ATP-pyrophosphate exchange assay in the presence and in the absence of a candidate inhibitor (Calendar, R. and Berg, P., Biochemistry 5:1690–1695 (1966)). In this reaction, the enzymatic synthesis of ATP from AMP and pyrophosphate in the absence of tRNA is monitored. A candidate inhibitor can be added to a suitable reaction mixture (e.g., 100 mM Tris-HCl, pH 7.5/5 mM $MgCl_2$/10 mM 2-mercaptoethanol/10 mM KF/2 mM ATP/2mM [$^{32}$P]pyrophosphate/1 mM tyrosine), and the mixture is incubated at 25° C. TyrRS (to a final concentration of ~10 nM) is added to initiate the reaction. Aliquots of the reaction are removed at various times and quenched in 7% (vol/vol) cold perchloric acid, followed by the addition of 3% (wt/vol) charcoal suspended in 0.5% HCl. The ATP adsorbed to charcoal is filtered onto glass fiber pads (Schleicher & Schuell), and formation of [$^{32}$P]ATP is quantified by liquid scintillation counting in Hydrofluor (National Diagnostics, Manville, N.J.). The enzyme activity measured in the presence of the compound can be compared with the activity in the absence of the compound to assess the level of inhibition. Alternatively, a candidate inhibitor can be preincubated with enzyme under suitable conditions. Preincubation in the absence of substrate provides a more sensitive assay for the detection of inhibition (e.g., detects slow binding inhibitors). For example, the compound can be added to a mixture containing ~10 nM tyrosyl-tRNA synthetase in 100 mM Tris-HCl, pH 7.5/5 mM $MgCl_2$/10 mM 2-mercaptoethanol/10 mM KF, and preincubated at 25° C. for 20 minutes. To initiate the reaction, ATP, [$^{32}$p] pyrophosphate and tyrosine are added to final concentrations of 2 mM, 2 mM and 1 mM, respectively. The reaction can be monitored as described above, and the activity measured in the presence of compound is compared with the activity in the absence of compound to assess the level of inhibition.

In another embodiment, formation of the aminoacylated tRNA is monitored in a standard aminoacylation assay. Inhibitors identified by enzymatic assay can be further assessed for antimicrobial activity using tester strains as described herein, or using other suitable assays. For example, the extent of aminoacylation of tRNA with tyrosine catalyzed by TyrRS (e.g., a GST fusion) can be measured by monitoring the incorporation of [$^{3}$H]tyrosine into trichloroacetic acid-precipitable [$^{3}$H]tyrosyl-tRNA in the presence of a candidate inhibitor, as compared with activity in the absence inhibitor. Appropriately diluted TyrRS can be preincubated for 20 minutes at 25° C. in, for example, 50 mM HEPES, pH 7.5/0.1 mg/ml BSA (bovine serum albumin)/10 mM $MgCl_2$/10 mM 2-mercaptoethanol/20 mM KCl/1–20% DMSO (preferably about 1%) in the presence or absence of a compound to be tested. The preincubation mixture can be supplemented with ATP, [$^{3}$H] tyrosine and tRNA to final concentrations of, for example, 4 mM ATP/20 $\mu$M [$^{3}$H]tyrosine (0.6 $\mu$Ci), and 90 $\mu$M crude tRNA or 2 $\mu$M specific $tRNA^{Tyr}$. The reaction is maintained at 25° C., and aliquots are removed at specific times, and applied to filter paper discs (3MM, Whatman) that have been presoaked with 5% (wt/vol) trichloroacetic acid. Filters are washed for three 10-minute periods in 5% trichloroacetic acid, rinsed in 95% ethanol and 100% ether, and the incorporation of $^{3}$H-tyrosine into tRNA (formation of $^{3}$H-Tyr-tRNA) can be measured in Betafluor by liquid scintillation counting. The aminoacylation assay can also be performed without preincubation under suitable conditions (e.g., using ~0.4 nM TyrRS in a reaction mixture containing 50 mM HEPES, pH 7.5/0.1 mg/ml BSA (bovine serum albumin)/10 mM $MgCl_2$/10 mM, 2-mercaptoethanol/20 mM KCl/1–20% DMSO/4 mM ATP/20 $\mu$M [$^{3}$H]tyrosine (0.6 $\mu$Ci), and 90 $\mu$M crude tRNA or 2 $\mu$M specific $tRNA^{Tyr}$) in the presence or absence of test compound. An $IC_{50}$ value (the concentration of inhibitor causing 50% inhibition of enzyme activity) for a known amount of active TyrRS can be determined.

Binding Assay

An isolated, recombinant aaRS or a portion thereof, and suitable fusion proteins can be used in a method to select and identify compounds which bind specifically to Candida TyrRSs, such as C. albicans tyrosyl-tRNA synthetase, and which are potential inhibitors of TyrRS activity. Compounds selected by the method can be further assessed for their inhibitory effect on TyrRS activity and for antimicrobial activity.

In one embodiment, an isolated or purified Candida TyrRS can be immobilized on a suitable affinity matrix by standard techniques, such as chemical cross-linking, or via an antibody raised against the isolated or purified TyrRS, and bound to a solid support. The matrix can be packed in a column or other suitable container and is then contacted with one or more compounds (e.g., a mixture) to be tested under conditions suitable for binding of compound to the TyrRS. For example, a solution containing compounds can be made to flow through the matrix. The matrix can be washed with a suitable wash buffer to remove unbound compounds and non-specifically bound compounds. Compounds which remain bound can be released by a suitable elution buffer. For example, a change in the ionic strength or pH of the elution buffer can lead to a release of compounds. Alternatively, the elution buffer can comprise a release component or components designed to disrupt binding of compounds (e.g., one or more substrates or substrate analogs which can disrupt binding of compound to the TyrRS, such as tyrosine, ATP, $tRNA^{Tyr}$, or other suitable molecules which competitively inhibit binding).

Fusion proteins comprising all of, or a portion of, the TyrRS linked to a second moiety not occurring in the Candida TyrRS as found in nature (see above), can be prepared for use in another embodiment of the method. Suitable fusion proteins for this purpose include those in which the second moiety comprises an affinity ligand (e.g., an enzyme, antigen, epitope). The fusion proteins can be produced by the insertion of a TyrRS gene or portion thereof into a suitable expression vector, which encodes an affinity ligand (e.g., pGEX-4T-2 and pET-15b, encoding glutathione S-transferase and His-Tag affinity ligands, respectively). The expression vector can be introduced into a suitable host cell for expression. Host cells are lysed and the lysate, containing fusion protein, can be bound to a suitable affinity matrix by contacting the lysate with an affinity matrix under conditions sufficient for binding of the affinity ligand portion of the fusion protein to the affinity matrix.

In one aspect of this embodiment, the fusion protein can be immobilized on a suitable affinity matrix under conditions sufficient to bind the affinity ligand portion of the fusion protein to the matrix, and is contacted with one or more compounds (e.g., a mixture) to be tested, under conditions suitable for binding of compounds to the TyrRS portion of the bound fusion protein. Next, the affinity matrix with bound fusion protein can be washed with a suitable wash buffer to remove unbound compounds and non-specifically bound compounds. Compounds which remain bound can be released by contacting the affinity matrix with fusion protein bound thereto with a suitable elution buffer (a compound elution buffer). Wash buffer can be formulated to permit binding of the fusion protein to the affinity matrix, without significantly disrupting binding of specifically bound compounds. In this aspect, compound elution buffer can be formulated to permit retention of the fusion protein by the affinity matrix, but can be formulated to interfere with binding of the compound(s) tested to the TyrRS portion of the fusion protein. For example, a change in the ionic strength or pH of the elution buffer can lead to release of compounds, or the elution buffer can comprise a release component or components designed to disrupt binding of compounds to the TyrRS portion of the fusion protein (e.g., one or more substrates or substrate analogs which can disrupt binding of compounds to the TyrRS portion of the fusion protein, such as tyrosine, ATP, or tRNA$^{Tyr}$, or other suitable molecules which competitively inhibit binding).

Immobilization can be performed prior to, simultaneous with, or after contacting the fusion protein with compound, as appropriate. Various permutations of the method are possible, depending upon factors such as the compounds tested, the affinity matrix-ligand pair selected, and elution buffer formulation. For example, after the wash step, fusion protein with compound bound thereto can be eluted from the affinity matrix with a suitable elution buffer (a matrix elution buffer, such as glutathione for a GST fusion). Where the fusion protein comprises a cleavable linker, such as a thrombin cleavage site, cleavage from the affinity ligand can release a portion of the fusion with compound bound thereto. Bound compound can then be released from the fusion protein or its cleavage product by an appropriate method, such as extraction.

To enrich for specific binding to the TyrRS portion of the fusion protein, compounds can be pre-treated, for example with affinity matrix alone, with affinity ligand or a portion thereof (e.g., the portion present in the fusion protein), either alone or bound to matrix, under conditions suitable for binding of compound to the TyrRS portion of the bound fusion protein.

One or more compounds can be tested simultaneously according to the method. Where a mixture of compounds is tested, the compounds selected by the foregoing processes can be separated (as appropriate) and identified by suitable methods (e.g., PCR, sequencing, chromatography). Large combinatorial libraries of compounds (e.g., organic compounds, peptides, nucleic acids) produced by combinatorial chemical synthesis or other methods can be tested (see e.g., Ohlmeyer, M. H. J., et al., Proc. Natl. Acad. Sci. USA 90:10922–10926 (1993) and DeWitt, S. H., et al., Proc. Natl. Acad. Sci. USA 90:6909–6913 (1993), relating to tagged compounds; see also Rebek, et al., Process for Creating Molecular Diversity, U.S. Ser. No. 08/180,215, filed Jan. 12, 1994, relating to compounds without tags; see also, Rutter, W. J., et al., U.S. Pat. No. 5,010,175; Huebner, V. D., et al., U.S. Pat. No. 5,182,366; and Geysen, H. M., U.S. Pat. No. 4,833,092). Where compounds selected from a combinatorial library by the present method carry unique tags, identification of individual compounds by chromatographic methods is possible. Where compounds do not carry tags, chromatographic separation, followed by mass spectrophotometry to ascertain structure, can be used to identify individual compounds selected by the method, for example.

Random sequence RNA and DNA libraries (see Ellington, A. D., et al., Nature 346: 818–822 (1990); Bock, L. C., et al., Nature 355: 584–566 (1992); and Szostak, J. W., Trends in Biochem. Sci. 17:89–93 (March, 1992)) can also be screened according to the present method to select RNA or DNA molecules which bind to a Candida TyrRS. Such molecules can be further assessed for antimicrobial effect upon introduction into a cell (e.g., by expression in the case of an RNA molecule selected by the method).

Tester Strains

Nucleic acids of the present invention can also be used in constructing tester strains for in vivo assays of the effect on the activity of the Candida enzyme of a substance which is added to tester strain cells. A tester strain comprises a host cell having a defect in a gene encoding an endogenous aaRS, and a heterologous aaRS gene which complements the defect in the host cell gene. Thus, complementation of a particular defective host cell aaRS gene by a heterologous aaRS gene is a threshold requirement for a tester strain. Because the aaRS genes are essential, the heterologous gene can be introduced into the host cell simultaneously with inactivation of the host cell gene to preserve viability. Alternatively, the heterologous gene can be introduced into the host cell before inactivation or loss of the host cell gene. In this case, to test for complementation, the host cell is then subjected to some change in conditions (e.g., a change in temperature, growth medium, selection conditions) which causes inactivation or loss of either the host aaRS gene or gene product, or both.

If the heterologous gene complements the inactivated host cell gene, such a cell can be used to determine whether a substance that is introduced into the cells for testing, can interact specifically with the heterologous tRNA synthetase (or a component in the pathway of the expression of the heterologous tRNA synthetase gene) to cause loss of function of the tested heterologous tRNA synthetase in those host cells. Thus, such cells are "tester strains". Successful cross-species complementation has been described, for example, for yeast seryl-tRNA synthetase and for yeast isoleucyl-tRNA synthetase in E. coli (Weygand-Durasevic, I., et al., Eur. J. Biochem 214:869–877 (1993); Racher, K. I., et al., J. Biol. Chem. 266:17158–17164 (1991)).

In tester cells to be used in an assay for chemical substances that can inhibit the function of a specific aaRS, the gene for the aminoacyl-tRNA synthetase can, for example, physically replace the host cell aaRS gene or can be present in addition to a host aaRS gene that does not produce a functional product, and the heterologous gene whose gene product is to be tested complements the host gene. A substance to be tested is administered to the tester cells, and the viability or growth of such cells can be compared with that of cells of a suitable control.

As a tester strain comprises a host cell comprising a heterologous aaRS gene (i.e., one from a heterologous species), a suitable host cell is heterologous with respect to the species from which the gene to be tested is isolated. For instance, suitable host cells to test *Candida albicans* genes can be host cells of a species other than *C. albicans*. Examples of species which are suitable for use as hosts for the construction of tester strains are *E. coli, B. subtilis*, and *S. cerevisiae*. These species are especially amenable to genetic manipulation because of their history of extensive study.

Suitable host cells having a genotype useful for the construction of a tester strain can be constructed or selected using known methods. For example, both in *E. coli* and in *S. cerevisiae*, a first plasmid which contains a functional copy of a host chromosomal aaRS gene (which is to be inactivated later), and some selectable marker gene, can be constructed and introduced into cells. Then, an inactivating mutation can be caused in the chromosomal copy of the aaRS gene.

This can be accomplished, for instance, by causing or selecting for a double crossover event which creates a deletion and insertion. This can be done by introducing into the cells double-stranded DNA having regions of homology to the DNA flanking the target aaRS gene, and having between these regions a gene encoding a selectable marker, either on a suitable vector or as a DNA fragment, as appropriate (Jasin, et al., U.S. Pat. No. 4,713,337; Schimmel, P., U.S. Pat. No. 4,963,487; Toth, M. J. and Schimmel, P., *J. Biol. Chem.* 261:6643–6646 (1986); Rothstein, R., *Methods in Enzymology* 194:281–301 (1991)). Such an approach simultaneously inserts a selectable marker and results in a deletion of the endogenous gene between the flanking sequences provided. Where needed to maintain viability, a compatible maintenance plasmid is provided encoding an endogenous or complementing aaRS.

A test plasmid which is compatible with the maintenance plasmid, and which contains the aaRS gene to be tested for complementation, can be introduced into the host cells. If the first plasmid has been constructed to have a mechanism to allow for inhibition of its replication (for example, a temperature sensitive replicon) or to have a mechanism by which cells containing the first plasmid can be selected against (by, for example, the use of 5-fluoroorotic acid to select against *S. cerevisiae* cells which have a first plasmid containing the URA3 gene), cells which survive by virtue of having a complementing aaRS gene on the second plasmid can be selected (Sikorsky, R. S. and Boeke, J. D., *Methods in Enzymology* 194:302–318 (1991)).

Causing or selecting for a double crossover event which creates a deletion and insertion can be used in itself as a one-step method of constructing a tester strain in which a native aaRS gene is replaced by the corresponding foreign gene whose gene product is to be tested. Endogenous recombination mechanisms have been used to advantage previously in *E. coli, B. subtilis*, and *S. cerevisiae*, among other organisms. This method depends on the ability of the heterologous gene to be tested to complement the native corresponding aaRS gene. This can be done by introducing into the cells double-stranded DNA having regions of homology to the DNA flanking the target native aaRS gene, and having between these regions a gene encoding a selectable marker as well as the heterologous aaRS gene intended to replace the native aaRS gene. The survival of cells expressing the selectable marker is indicative of expression of the introduced heterologous aaRS gene and complementation of the defect in the endogenous synthetase.

For example, a tester strain useful for testing the effect of a compound on the function of TyrRS expressed by an inserted *C. albicans* gene, can be constructed in a one-step method in a suitable host cell. Optional positive and negative controls for this cross-species transformation can be used to show that the resulting strain depends on the TyrRS gene from *C. albicans* for growth and that this recombination event is not lethal. For example, *S. cerevisiae* cells can be transformed with a suitable construct, such as a linearized plasmid containing an insert. Generally, the construct includes a selectable marker gene for antibiotic resistance, or other suitable selectable marker. In one embodiment, a linearized plasmid which contains the *C. albicans* TyrRS gene and an antibiotic resistance gene, situated between sequences homologous to the flanking sequences of the endogenous TyrRS gene of the host cells, is used to transform the host cell. For a positive control, the linearized plasmid can be constructed in a similar fashion, except that the native *S. cerevisiae* TyrRS gene replaces the *C. albicans* gene, such that a normal *S. cerevisiae* TyrRS gene is located adjacent to the antibiotic resistance marker in the insert. As a negative control, the insert can be designed to contain only the flanking sequences and the antibiotic resistance marker, for example. Antibiotic resistant transformants are not expected upon transformation with the negative control construct, as homologous recombination with the construct results in deletion of the endogenous TyrRS gene. Successful construction of a tester strain can also be confirmed by Southern analysis.

In cases of gene duplication (LysU and LysS in *E. coli* a (Kawakami, K., et al., *Mol. Gen. Genet.* 219:333–340 (1989); Leveque, F., et al., *Nucleic Acids Res.* 18:305–312 (1990); Clark, R. L. and Neidhardt, F. C., *J. Bacteriol.* 172:3237–3243 (1990)), or the presence of a cryptic gene (tyrZ in *B. subtilis*, Glaser, P., et al., DNA *Sequ. and Mapping* 1:251–61 (1990); Henkin, T. M., et al., *J. Bacteriol.* 174:1299–1306 (1992), a suitable tester strain can be constructed by simultaneous inactivation of both of the host genes, or by sequential inactivation. For instance, inactivation of one host gene by a suitable method, such as by insertion of a selectable marker, can be followed by a one-step gene replacement of the remaining host gene with a heterologous Candida aaRS gene and a second selectable marker.

The yeast *S. cerevisiae* offers additional possibilities for genetic manipulations to create tester strains, relative to bacteria. Yeast integrating plasmids, which lack a yeast origin of replication, can be used for making alterations in the host chromosome (Sikorski, R. S. and Heiter, P., *Genetics* 122:19–27 (1989); Gietz, R. D. and Sugino, A., *Gene* 74:527–534 (1988)). In another embodiment, one-step gene disruptions can be performed in diploid cells using a DNA fragment comprising a copy of an aaRS gene (optionally containing a deletion in the aaRS gene) having an insertion of a selectable marker in the aaRS gene. A suitable fragment can be introduced into a diploid cell to disrupt a chromosomal copy of the yeast gene. Successful integration of the disrupted aaRS gene can be confirmed by Southern blotting and by tetrad analysis of the sporulated diploid cells. The diploid cells heterozygous for the disrupted aaRS gene provide a diploid host strain which can be transformed with a plasmid containing the heterologous aaRS gene. These cells can be sporulated and the haploid spores analyzed for rescue of the defective chromosomal aaRS by the heterologous aaRS gene.

Alternatively, those diploid cells that are found to contain one copy of the disrupted chromosomal aaRS gene, as well as one functional copy, can be transformed with a maintenance plasmid which contains a gene which complements the disruption, such as the corresponding wild type yeast aaRS gene, and which provides for a mechanism to select against survival of the cells containing this plasmid. These cells can then be made to sporulate to obtain a haploid null strain containing the disrupted chromosomal aaRS gene and the wild type gene on the maintenance plasmid. This haploid host strain can then be transformed with a test plasmid which expresses a heterologous aaRS gene, and the maintenance plasmid can be selected against by growing this strain under appropriate conditions.

Construction of a tester strain may start with the isolation of a mutant host strain which produces, for example, an inactive tRNA synthetase specific for a particular amino acid, a tRNA synthetase which is conditionally inactivatible, or which carries a chromosomal deletion of a tRNA synthetase. A number of *E. coli* and *S. cerevisiae* strains have been described that can be used for constructing tester strains. Some of these strains are described below for illustrative purposes. The procedures used to isolate and/or construct these *E. coli* and *S. cerevisiae* strains, or similar procedures, can be used or adapted to make additional mutant strains in *E. coli*, *S. cerevisiae* or other host organisms.

*E. coli* strains having a defect, such as a null mutation, in an aminoacyl-tRNA synthetase gene can be constructed using a cloned *E. coli* aaRS gene. Each aminoacyl-tRNA synthetase from *E. coli* has been cloned (see Meinnel, T., et al., 1995, "Aminoacyl-tRNA Synthetases: Occurrence, Structure and Function," In: tRNA: Structure, Biosynthesis and Function, Söll,D. and RajBhandary, U., Eds., (American Society for Microbiology: Washington, D.C.), Chapter 14, pp. 251–292, the teachings of which are incorporated herein by reference). The cloned genes can be incorporated into a suitable construct and be used as maintenance plasmids in a suitable host cell.

A number of *E. coli* strains have been characterized in which an aaRS gene has been inactivated by some method, in whole or in part, yielding an observable phenotypic defect which can be detectably complemented. For example, null strains in which the gene encoding IleRS has been inactivated (IQ843, IQ844, see Shiba, K. and Schimmel, P., *J. Biol. Chem.* 267:22703–22706 (1992)), and a mutant strain (MI1, see Starzyk, et al., *Science* 237:1614–1618 (1987) and Iaccarino and Berg, *J. Bacteriol.* 105:527–537 (1970)) having an isoleucine auxotrophy due to an elevated $K_m$ for isoleucine of the enzyme encoded by the chromosomal ileS allele, have been described.

*E. coli* strain IQ843/pRMS711 and its derivative IQ844/pRMS711 contain a chromosomal deletion of the ileS gene (ΔileS203::kan), and are propagated by expression of wild type IleRS at 30° C. from a temperature-sensitive maintenance plasmid designated pRMS711, which encodes the wild type ileS gene and a gene which confers chloramphenicol resistance. pRMS711 cannot replicate at 42° C., thus, at the non-permissive temperature, the maintenance plasmid is lost. Following the introduction of a test construct into these strains, the growth of chloramphenicol sensitive colonies at a non-permissive temperature (e.g., 42° C.) is indicative of complementation of the chromosomal ileS deletion by the introduced construct (Shiba, K. and Schimmel, P., *Proc.* *Natl. Acad. Sci. USA* 89:1880–1884 (1992); Shiba, K. and Schimmel, P., *Proc. Natl. Acad. Sci. USA* 89:9964–9968 (1992); Shiba, K. and Schimmel, P., *J. Biol. Chem.* 267:22703–22706 (1992)).

Temperature sensitive alleles are examples of genes encoding conditionally inactivatable tRNA synthetases. For example, temperature-sensitive alleles of the genes encoding cytoplasmic IleRS (ils1-1) and MetRS (mes1-1) have been described in *S. cerevisiae* (Hartwell, L. H., and McLaughlin, C. S., *J. Bacteriol.* 96:1664–1671 (1968); McLaughlin, C. S., and Hartwell, L. H., *Genetics* 61:557–566 (1969)), and are available from the Yeast Genetic Stock Center (University of California-Berkeley; catalog nos. 341 and 19:3:4, respectively).

The *S. cerevisiae* genome has been fully sequenced and all of the aminoacyl-tRNA synthetases have been identified. The KRS1 gene was shown to be essential by the construction of a disrupted allele of KRS1 (Martinez, R., et al., *Mol. Gen. Genet.* 227:149–154 (1991). For construction of a tester strain in *S. cerevisiae*, a plasmid such as the one reported by P. Walter, et al. (*Proc. Natl. Acad. Sci. USA* 80:2437–2441, (1983)), which contains the wild type cytoplasmic methionyl-tRNA synthetase gene of S. cerevisiae, MES1, can be used to construct mes1 strains, and for the construction of maintenance plasmids to create cytoplasmic tester strains for a MetRS (see also Fasiolo, F., et al., *J. Biol. Chem.* 260:15571–15576 (1985)).

Strains having a defect in mitochondrial aminoacyl-tRNA synthetase can be constructed using a cloned mitochondrial aaRS gene, and used to make tester strains (see Meinnel, T. et al., 1995, "Aminoacyl-tRNA synthetases: Occurrence, Structure and Function", In: *tRNA: Structure, Biosynthesis and Function*, Söll,D. and RajBhandary, U, Eds., American Society for Microbiology: Washington, D.C., Chapter 14, pp. 251–292; also see ATCC Catalog of Recombinant DNA Materials, American Type Culture Collection, Rockville, Md., regarding mitochondrial aaRS genes. For example, an *S. cerevisiae* strain has been constructed which carries a disruption of MSY1, the gene encoding mitochondrial tyrosyl-tRNA synthetase. Plasmids carrying MSY1 which rescue this defect, also have been constructed (Hill, J. and Tzagoloff, A., Columbia University; see Edwards, H. and Schimmel, P., *Cell* 51:643–649 (1987)).

In *S. cerevisiae*, to construct a maintenance plasmid or a test plasmid carrying a heterologous gene, a suitable vector, such as a yeast centromere plasmid (CEN; single-copy) or 2μ vector (high copy) can be used. A heterologous gene to be tested can also be incorporated into the chromosome, using an integrating plasmid, for example. Examples of convenient yeast vectors for cloning include vectors such as those in the pRS series (integrating, CEN, or 2μ plasmids differing in the selectable marker (HIS3, TRP1, LEU2, URA3); see Christianson, T. W., et al., *Gene* 110:119–122 (1992) regarding 2μ vectors; see Sikorski, R. S. and Hieter, P., *Genetics* 122:19–27 (1989) regarding integrating and CEN plasmids which are available from Stratagene, La Jolla)) and shuttle vectors (integrating, CEN or 2μ vectors) which contain the multiple cloning site of pUC19 (Gietz, R. D. and Sugino, A., *Gene* 74:527–534 (1988)). Examples of expression vectors include pEG (Mitchell, D. A., et al., *Yeast* 9:715–723 (1993)) and pDAD1 and pDAD2, which contain a GAL1 promoter (Davis, L. I. and Fink, G. R., *Cell* 61:965–978 (1990)).

A variety of promoters are suitable for expression. Available yeast vectors offer a choice of promoters. In one embodiment, the inducible GAL1 promoter is used. In another embodiment, the constitutive ADH1 promoter (alcohol dehydrogenase; Bennetzen, J. L. and Hall, B. D., *J. Biol. Chem.* 257:3026–3031 (1982)) can be used to express an inserted gene on glucose-containing media. An example of a vector suitable for expression of a heterologous aaRS gene in yeast is pQB169 (Example 8).

For illustration, a yeast tester strain can be constructed as follows. A *Saccharomyces cerevisiae* strain with convenient markers, such as FY83 (MATa/MATα lys2-128δ/lys2-128δ leu2Δ1/leu2Δ1 ura3-52/ura3-52 trp1Δ63/trp1Δ63) can be used as a host cell.

A nucleic acid encoding a yeast cytoplasmic aaRS can be used to create a null allele of the yeast cytoplasmic aaRS gene. For example, a deletion/insertion allele can be constructed by excising the aaRS open reading frame, including the promoter region and 3' flanking region or portions thereof from a cloned gene, and replacing the excised sequence with a selectable marker (e.g., TRP1). This aaRS::TRP1 fragment can be used to transform the diploid strain FY83, and Trp$^+$ transformants can be selected (Rothstein, J., Methods in Enzymol. 101:202–211 (1983)). Standard genetic procedures can be employed to identify the appropriate integrant created by this one-step gene disruption (a diploid having the genotype MATa/MATα lys2-128δ/lys2-128δleu2Δ1/leu2Δ1 ura3-52/ura3-52 trp1Δ63/trp1Δ63 aaRS::TRP1/aaRS); Rose, M. D., et al., Methods in Yeast Genetics, 1990, Cold Spring Harbor Press, Cold Spring Harbor, N.Y.).

To construct a maintenance plasmid, a fragment containing the aaRS coding region, its promoter and some of the 3' untranslated region (e.g., a region approximately equivalent to that deleted in the construction of the null allele above) can be excised and introduced into a vector such as YCplac33, a CEN plasmid containing a URA3 selectable marker (Gietz, R. D. and Sugino, A., Gene 74:527–534 (1988)). The resulting plasmid can be used to transform the aaRS::TRP1/aaRS diploid described above, and Ura$^+$ transformants which contain the maintenance plasmid can be selected. The resulting diploid can be sporulated and a haploid Trp$^+$Ura$^+$ spore (an aaRS null strain), corresponding to a aaRS::TRP1 strain dependent upon the URA3- aaRS maintenance plasmid can be isolated.

To construct a test plasmid (a plasmid bearing a heterologous tRNA synthetase gene to be tested for its ability to complement the defect in the endogenous yeast gene), a heterologous aaRS gene to be tested can be inserted into a suitable vector for expression. For instance, the multicopy vector pQB169 described in Example 8 can be used. A fragment containing the *C. albicans* aaRS gene can be inserted into pQB169, using one or more suitable restriction sites in the multiple cloning site, for example. Alternatively, to test whether a relatively reduced level of expression of the heterologous tRNA synthetase gene permits complementation, a fragment containing the *C. albicans* aaRS gene can be inserted into a CEN plasmid such as pQB172 (Example 8) for expression. Preferably, the heterologous gene is inserted into the vector so that its ATG start codon is the first ATG within 50 to 100 bp of the transcription start site of the ADH promoter of the vector.

Because these plasmids bear the LEU2 selectable marker, they can be used to transform a null strain, such as the Trp$^+$Ura$^+$Leu- strain described, and Leu$^+$ transformants containing the test plasmid can be selected. Leu$^+$Ura$^+$Trp$^+$ transformants (containing a aaRS::TRP1 allele, a URA3 maintenance plasmid, and the LEU2 test plasmid) can be tested for growth on media containing 5-fluoroorotic acid (5-FOA). 5-FOA is toxic to URA3 cells, and causes loss of the URA3 maintenance plasmid (Boeke, J., et al., *Mol. Gen. Genet.* 197:345–346 (1984)). Accordingly, growth of cells on media containing 5-FOA is indicative of complementation of the lethal deletion in the aaRS gene on the chromosome (aaRS::TRP1) by the heterologous aaRS gene on the test plasmid. Cells that are unable to grow on 5-FOA are dependent upon the maintenance plasmid for viability, and therefore, are indicative of insufficient activity to complement the lethal deletion in the aaRS gene. Where complementation is observed, the strain can be used to test for inhibitors of the product of the heterologous gene encoded by the test plasmid.

In another embodiment, a eucaryotic host cell is used to construct a mitochondrial tester strain. For example, in yeast, each of the mitochondrial tRNA synthetases is essential for growth on non-fermentable carbon sources (e.g., glycerol). Thus, complementation tests can be conducted in mitochondrial tester strains. As the genes encoding mitochondrial aminoacyl-tRNA synthetases are typically nuclear-encoded, the procedures described above can be modified to construct mitochondrial tester strains having a defect in a mitochondrial aminoacyl-tRNA synthetase. Modification is necessitated by the fact that yeast strains with a defect in mitochondrial protein synthesis, such as a defective aminoacyl-tRNA synthetase, lose their mitochondrial DNA, rapidly becoming rho$^-$. As a result, these strains are unable to grow on non-fermentable carbon sources even if a complementing gene is introduced into the strain. Therefore, in a haploid strain having a defect in, for example, the yeast mitochondrial tyrosyl-tRNA synthetase gene (e.g., a gene disruption with a cosegregating selectable marker constructed as indicated above; see also Tzagoloff, A., et al., J. Biol. Chem. 263(2): 850–856 (1988)), the haploid strain can be crossed with a rho$^+$ strain having a wild-type mitochondrial tyrosyl-tRNA synthetase gene to restore the mitochondrial DNA. The resulting rho$^+$ diploid can then be transformed with a plasmid which encodes the wild-type yeast mitochondrial tyrosyl-tRNA synthetase (i.e., a maintenance plasmid) and a second selectable marker. Following sporulation, progeny spores which carry the defective mitochondrial TyrRS, identified by the presence of the cosegregating selectable marker, and the maintenance plasmid, identified by the presence of the second selectable marker, and which are rho$^+$, can be isolated (e.g., by tetrad analysis). Strains constructed in this manner would be suitable for complementation assays using Candida tyrosyl-tRNA synthetases.

For instance, a plasmid encoding a Candida tyrosyl-tRNA synthetase gene can be introduced into such a strain on a second plasmid having a third selectable marker. As indicated above, the maintenance plasmid can be selected against (e.g., where the selectable marker is URA3, selection on 5-fluoroorotic acid leads to loss of the maintenance plasmid), and complementation by the Candida gene can be monitored on a non-fermentable carbon source.

In another embodiment, a mitochondrial tyrosyl-tRNA synthetase gene disruption with a cosegregating selectable marker can be constructed in a diploid rho$^+$ strain (see e.g., Edwards, H. and Schimmel, P., Cell 51:643–649 (1987)). A plasmid encoding a Candida tyrosyl-tRNA synthetase gene is introduced on a plasmid having a second selectable marker. Sporulation of a resulting diploid yields two progeny spores carrying the yeast mitochondrial tyrosyl-tRNA synthetase gene disruption, identified by the presence of a cosegregating selectable marker, and two progeny spores carrying the corresponding wild-type gene. The presence of the plasmid can be monitored by the presence of the second selectable marker. Complementation by the Candida gene on the introduced plasmid is indicated by growth on non-fermentable carbon sources of spores carrying the disrupted tyrosyl-tRNA synthetase gene.

In the case of a mitochondrial tester strain, the Candida aminoacyl-tRNA synthetase can be imported into mitochondria to achieve complementation of the mitochondrial defect. When it is necessary to achieve import or desirable to improve the efficiency of import of the aminoacyl-tRNA synthetase in the host cell, a gene fusion can be constructed using a sequence encoding a mitochondrial targeting sequence which functions in the host cell. For example, a mitochondrial targeting sequence can be introduced at the amino-terminal end of the Candida aminoacyl-tRNA synthetase. In one embodiment in yeast, the Candida aaRS gene or a sufficient portion thereof is introduced into a vector in which it is placed under the control of the minimal alcohol dehydrogenase promoter and is fused to the yeast cytochrome oxidase IV targeting signal derived from plasmid pMC4 (Bibus, et al., *J. Biol. Chem.* 263:13097 (1988)). Expression of the construct yields a fusion protein with an N-terminally located cytochrome oxidase IV targeting signal joined to the Candida aaRS protein.

If the construction methods described here are not successful initially, one or more natural or synthetic Candida or other (e.g., procaryotic, such as a bacterial, or eukaryotic, such as a mammalian or fungal) tRNA gene(s) can be introduced into the host cell to provide one or more cognate tRNAs for the Candida aaRS. The tRNA genes of a number of species have been cloned and sequenced (Steinberg, S., et al., "Compilation of tRNA sequences and sequences of tRNA genes", Nucleic Acids Res. 21:3011–3015 (1993)). A method for constructing a strain of *Streptomyces lividans* in which an essential tRNA gene has been inactivated in the chromosome, and the gene is instead maintained on a plasmid, has been described (Cohen, S. N., WO 94/08033 (1994)).

Use of Tester Strains

To assess the inhibitory effect of a substance on a tester strain, the cells are maintained under conditions suitable for complementation of the host cell defect, under which complementation of the host cell defect is dependent upon the test gene (i.e., assay conditions). A substance to be tested is administered to the tester cells, and the viability or growth of the tester cells can be compared with that of cells of one or more suitable controls. A variety of control experiments can be designed to assess the inhibitory effect of a substance and/or the specificity of inhibition. The following examples are provided for purposes of illustration.

A preliminary test for inhibitory effect may be conducted where desired. For example, a substance to be tested can be administered to tester cells maintained under assay conditions, and the viability or growth of the tester cells in the presence of the substance can be compared with that of tester cells maintained under the same conditions in the absence of the substance. If it is determined that the substance inhibits growth of the tester cells, a further assessment of the specificity of inhibition by the substance can be conducted as described below.

Alternatively, the inhibitory effect of a substance on tester cell growth and the specificity of inhibition can be determined without conducting the preliminary test for inhibitory activity. The following examples, in which the various cell types are in each case exposed to drug, are provided for purposes of illustration only.

To determine the specificity of inhibition, the viability or growth of the tester cells can be compared with that of cells of one or more suitable control strains maintained under the same conditions. In particular, tester strains and control strains are maintained under assay conditions, and exposed to the substance to be tested.

Strains which are similar to the tester strain, but lack the heterologous aminoacyl-tRNA synthetase gene present in the tester strain (i.e., the "test gene"), can serve as control strains. These control strains comprise a "control gene" which is an aminoacyl-tRNA synthetase gene other than the heterologous Candida aaRS gene present in the tester strain (i.e., an aaRS gene from a different species, such as a procaryotic or eukaryotic species). The control gene can be a cytoplasmic or mitochondrial aaRS gene, and it encodes an aaRS specific for the same amino acid as the aaRS encoded by the test gene. Viability or growth of the control strain is dependent upon the control gene under the conditions of the assay.

In one embodiment, a cell which is a cell of the same species as the host cell used to construct the tester strain, and which further comprises a control aaRS gene, is selected as a control. For example, the control gene can be a wild-type aaRS gene from the control strain species which encodes an aaRS specific for the same amino acid as the aaRS encoded by the test gene. Such a cell can be used when, for example, the substance or compound to be tested does not significantly affect growth of the control strain under the assay conditions. For example, where an *E. coli* host is used to construct a tester strain having a *C. albicans* aaRS gene, an *E. coli* strain having a wild-type *E. coli* control gene can be used as a control strain. As another example, if a yeast host cell having a defect in a mitochondrial aaRS gene is used to construct the tester strain, a yeast strain comprising the wild type mitochondrial gene can be used as a control strain.

In another embodiment, the control strain can be a strain distinct from the tester strain, which is constructed in a manner which generally parallels that of the tester strain comprising the test gene, such that complementation of the host cell defect, which is also present in the control strain, is dependent upon the control gene under the assay conditions. In this embodiment, the control strain preferably comprises a host cell of the same species as the host cell used to construct the tester strain, and is closely related in genotype to the tester strain. These preferred control strains comprise a "control gene," which, as indicated above, is an aaRS gene other than the test gene (i.e., an aaRS gene from a different species, such as a heterologous procaryotic or eukaryotic species). Furthermore, the control gene, which can be cytoplasmic or mitochondrial, encodes an aaRS specific for the same amino acid as the test gene. Preferably, the control gene is selected from a species which is a host for the pathogen from which the test gene is derived, permitting the identification of specific inhibitors which selectively inhibit the pathogen aaRS (e.g., human control gene for an *C. albicans* test gene). Alternatively, because the eukaryotic aminoacyl-tRNA synthetases are generally more closely related to each other than to procaryotic aminoacyl-tRNA synthetases, a control gene from another eukaryote (e.g., a different mammalian species) can be used in lieu of one selected from the host species (e.g., a rat or mouse control gene for an *C. albicans* test gene).

For example, a strain isogenic with a tester strain, except for the substitution of a human control gene, can serve as a control strain. Such a control strain can be constructed using the same methods and the same host cell used to construct the tester strain, with the exception that a human control gene is introduced into the host cell in lieu of the heterologous Candida aaRS gene present in the tester.

Under the conditions of this assay, growth or viability of the control strain is dependent upon the control aaRS gene, which complements the host cell aaRS defect in the control strain. Specific inhibition by a substance can be determined by comparing the viability or growth of the tester strain and control strain in the presence of the substance.

In some cases, further controls may be desired to assess specific inhibition. For this purpose, one or more additional "comparison control" strains are used for purposes of comparison. These additional controls can be used to assess the relative effects of a substance upon growth of the tester and control strains in the presence of the substance.

Strains useful for this purpose include, for example, strains of the same species as the host cell used to construct the tester strain, which contain a wild type version of the aaRS gene which is inactivated in the tester strain. In one embodiment, where an *E. coli* host is used to construct a tester strain comprising a *C. albicans* test gene, an *E. coli* strain comprising a wild-type *E. coli* aaRS gene can be used as a comparison control strain. In another embodiment, "parental-type" cells (e.g., parent host cells or a similar strain) are used as comparison controls. For example, the parent host cells of the tester strain can serve as a comparison control strain for the tester strain. Where the tester strain and the control strain have the same parent, a single strain can be used as the comparison control strain for both tester and control strains.

For example, a parent host cell from which the tester and control strains were both constructed (e.g., by inactivation and replacement of the wild type host aaRS gene) can be used as a comparison control strain. This comparison control strain contains a wild type version of the aaRS gene which is inactivated in the tester and control strains, and the viability or growth of this comparison control strain is dependent upon the wild type aaRS under the conditions of the assay. Specific inhibition of the heterologous Candida aaRS encoded by the test gene (or a step in the expression of the Candida gene) is indicated if, after administering the substance to the tester strain, growth of the tester strain is reduced as compared with an appropriate comparison control strain, and growth of the control strain is not reduced, or is relatively less reduced, as compared with its appropriate comparison control strain.

Testing for Antibiotic Resistance to tRNA Synthetase Inhibitors

Mutation of a drug target can reduce the effectiveness of antimicrobial or antibiotic agents, and can confer drug resistance. Thus, mutation of a target aminoacyl-tRNA synthetase, such as a *C. albicans* TyrRS, could reduce the effectiveness of an inhibitor of aaRS activity. To test for mutations that confer resistance to an inhibitor (e.g., an inhibitor of aaRS activity, including such an inhibitor having antimicrobial activity) a variety of approaches can be used. Mutant Candida aaRS genes can be obtained, for example, by isolation of a mutant gene, or by preparing an individual mutant gene or an expression library of mutant Candida aaRS genes, such as a library of mutants of a *C. albicans* TyrRS gene. The mutant gene or gene library can be introduced into suitable host cells for screening for resistance to a compound.

An isolated tRNA synthetase gene, such as a *C. albicans* aaRS gene, can be mutagenized by any suitable method including, but not limited to, cassette mutagenesis, PCR mutagenesis (e.g., the fidelity of PCR replication can be reduced to induce mutation by varying $Mg^{2+}$ concentration, increasing the number of amplification cycles, altering temperatures for annealing and elongation, to yield random mutants), or chemical mutagenesis (e.g., nitrosoguanidine, ethylmethane sulfonate (EMS), hydroxylamine) of the entire gene or a portion thereof. The mutagenesis products can be used to construct an expression library of mutant genes (e.g., by inserting the gene into an expression vector, or replacing a portion of an expression vector comprising the wild-type gene with mutant fragments) which is introduced into a host cell.

In one embodiment, if the inhibitor is known to inhibit the host cell (e.g., *E. coli*, yeast, *Bacillus subtilis*) aminoacyl-tRNA synthetase specific for the same amino acid, the mutant genes can be introduced into the wild-type host and the resulting cells can be exposed to drug to assess resistance.

In another embodiment, the procedures described above relating to tester strains are used in the method to identify mutants resistant to inhibitor. Introduction of the heterologous mutant aaRS gene(s) (i.e., mutant test gene(s)) into a host cell is carried out as described above for the production of tester strains. Using MetRS as an example, the library can be introduced into a host cell having a defect in the endogenous gene encoding MetRS. The metG null strain of *E. coli* designated MN9261/pRMS615 is an example of the type of strain that can be constructed and used as a host for the introduction of mutant Candida aaRS gene(s) (in that case, MetRS genes; see Kim, et al., *Proc. Natl. Acad. Sci. USA* 90:10046–10050 (1993), describing a strain which carries a null allele of metG, and a temperature sensitive maintenance plasmid, carring a wild type metG allele (encoding *E. coli*MetRS) and having a temperature sensitive replicon which causes loss of the maintenance plasmid at the non-permissive temperature).

Active, drug-resistant mutants are then identified by a selection process in which cells containing mutant genes encoding active aaRS are identified, and the effect of an inhibitor upon aaRS activity is assessed. Cells are maintained under conditions suitable for expression of the mutated gene, and cells containing an active mutant aaRS (e.g., an active recombinant *C. albicans* TyrRS) are identified by complementation of the host cell defect. Where complementation occurs, each resulting transformant is, in essence, a tester strain comprising a mutant test gene. Cells containing active mutant aaRS as determined by complementation of the host cell defect are then exposed to inhibitor, and the effect of inhibitor on cell growth or viability is assessed to determine whether the active mutant aaRS further confers resistance to inhibitor.

In the case of the metG null strain, complementation by the Candida gene is indicated by growth at the non-permissive temperature at which the maintenance plasmid is lost. Cells which survive loss of the maintenance plasmid due to the presence of the complementing mutant gene are then challenged with inhibitor to assess resistance. Resistance can be assessed by comparison to a suitable control by methods analogous to those described above for determining inhibition and/or the specificity of inhibition of a substance in tester cells. For example, the relative effects of an inhibitor upon a tester strain comprising the mutant test gene and upon a tester strain differing only in that it contains the test gene lacking the mutation, can be assessed by comparing the viability or growth of cells which are dependent upon either the test gene or mutant test gene for growth under conditions suitable for complementation of the host cell defect. For instance, the effect of inhibitor on the protein encoded by the test gene lacking the mutation can be determined by comparing the growth of cells containing the test gene in the presence of drug to the growth of such cells in the absence of drug, and the effect of inhibitor on the protein encoded by a mutant test gene can be determined by comparing growth of cells containing the mutant test gene in the presence of drug to the growth of such cells in the absence of drug. A decrease in the inhibitory effect on growth of cells carrying the mutant test gene as compared to the inhibitory effect against cells carrying the test gene lacking the mutation is indicative of resistance.

Cells containing a complementing mutant test gene which further confers resistance to an inhibitor can be used to identify derivatives of the inhibitor with improved antimicrobial effect, which circumvent resistance. Such cells can also be used to identify additional inhibitors having inhibitory activity against the active mutant aaRS encoded by the mutant test gene.

In another embodiment, a naturally occurring mutant Candida aaRS gene which confers resistance to an inhibitor upon a Candida cell, can be isolated from the Candida organism using nucleic acids of the present invention as probes. The cloned gene can then be introduced into a host cell as described for the production of tester strains. Tester cells comprising the mutant test gene which confers resistance, and which complements the host defect, can be used as described herein to identify additional inhibitors having reduced susceptibility to the resistance mutation or derivatives of the inhibitor with improved inhibitory activity.

Vectors carrying mutant genes which confer resistance to inhibitor can be recovered and the insert analyzed to locate and identify the mutation by standard techniques, such as DNA sequence analysis, to yield additional information regarding the nature of mutations capable of conferring resistance to selected inhibitors. Mutant proteins can also be expressed and purified for further characterization by in vitro kinetic and binding assays.

Applications in Biochemistry

The Candida tyrosyl-tRNA synthetase or stable subdomains of the protein can be used in a method to separate tyrosine from a mixture of tyrosine and other compounds such as other amino acids, or to specifically isolate L-tyrosine from D-tyrosine. The tyrosyl-tRNA synthetase can be chemically attached to a solid support material packed in a column or other suitable container. Alternatively, a fusion protein, such as a GST-tRNA synthetase fusion or a His tag-tRNA synthetase fusion (having a histidine hexamer tail), can permit attachment to a suitable solid support which binds the GST portion or His tag portion of the fusion protein, respectively. For example, a mixture of tyrosine and other compounds can be loaded onto a column under conditions in which tyrosine binds to tyrosyl-tRNA synthetase, while other compounds present in the mixture flow through the column. In a later step, tyrosine can be released from tyrosyl-tRNA synthetase by changing the conditions in the column, such as washing with a solution of high ionic strength to elute L-tyrosine, for example.

In a similar manner, the tyrosyl-tRNA synthetase can be used in a method to isolate tRNA that is specifically recognized by the tRNA synthetase.

The Candida tyrosyl-tRNA synthetase can be used in the quantitative determination of tyrosine by its conversion to the corresponding aminoacyl-hydroxamate (tyrosyl-hydroxamate). An example of an appropriate assay is illustrated by the following series of reactions.

tyrosine+ATP→tyrosine—AMP+PP$_i$ (in the presence of excess pyrophosphatase and ATP at pH 7.5, where pyrophosphatase catalyzes the conversion of the product inorganic pyrophospate (PP$_i$) to inorganic orthophosphate (P$_i$); ATP is adenosine triphospate; AMP is adenosine monophosphate)

tyrosine—AMP+NH$_2$OH→tyrosine—NHOH+AMP (at pH 7.5)
tyrosine—NHOH+FeCl$_3$→colored complex (at acidic pH)

The resulting colored complex can be quantitated by spectrophotometric measurements of absorbance at 540 nm, and compared with a standard curve made using known concentrations of tyrosine. This assay is based on the reactions described by Stulberg and Novelli, *Methods in Enzymology* 5:703–707 (1962).

The Candida tyrosyl-tRNA synthetases can also be used for the quantitative determination of ATP. In the presence of excess amino acid such as tyrosine, and in the presence of pyrophosphatase to convert the product PP$_i$ to P$_i$, the ATP is quantitatively converted to AMP and inorganic pyrophosphate by the tyrosyl-tRNA synthetase. For example, tyrosine+ATP tyrosine—AMP+PP$_i$ (in the presence of TyrRS)

PP$_i$+H$_2$O→2P$_i$ (in the presence of pyrophosphatase)

P$_i$ can be quantitated by reaction with molybdate, measuring the absorbance at 580 nm and comparing to a standard curve made using known quantities of orthophosphate.

Exemplification

The present invention will now be illustrated by the following Examples, which are not intended to be limiting in any way.

Materials and Methods

All restriction enzymes were purchased from New England Biolabs (Beverly, Mass.) unless otherwise stated. Ultrapure deoxynucleotide triphosphates (dNTPs) were purchased from Pharmacia. "Overnight" refers to more than 8 hours (up to 16 hours). Radioactive compounds were purchased from Dupont NEN. All bacterial transformations were done with the CaCl$_2$ procedure, unless otherwise stated. Sequencing was done using the Sequenase kit from USB. Procedures for standard techniques (e.g. bacterial transformation) and reagent preparation (e.g. TAE buffer) were as described in Sambrook, J., et al., *Molecular Cloning: A Laboratory Manual,* 2nd Ed., Cold Spring Harbor Laboratory, Cold Spring Harbor, N.Y. (1989). Media for yeast cultures and experimental techniques used for yeast manipulations were as described in *Methods in Yeast Genetics: A Laboratory Manual,* Rose, M. D., F. Winston and P. Hieter, eds., Cold Spring Harbor Laboratory Press, Cold Spring Harbor, N.Y. (1990).

Abbreviations

LB=Luria Broth; X-Gal=5-bromo-4-chloro-3-indolyl-β-D-galactoside; EDTA=ethylenediaminetetraacetic acid; DTT=dithiothreitol; PBS=phosphate buffered saline; BSA=bovine serum albumin; IPTG=isopropyl-β-D-thiogalactoside; 5-FOA=5-fluoroorotic acid; SDS=sodium dodecyl sulfate

EXAMPLE 1

PCR Amplification of DNA Fragments of Tyrosyl-tRNA Synthetase Genes from *C. albicans* Genomic DNA PCR was used to obtain amplified DNA fragments of tyrosyl-tRNA synthetase (TyrRS) genes using genomic DNA from *C. albicans* strain SC5314 as the template (Gillum, A. et al., *Mol. Gen. Genet.* 198:179–182 (1984); a gift of Brendan Cormack, Stanford University). The PCR primers were designed to contain coding sequences for highly conserved regions in TyrRSs. Conserved regions were found by aligning the amino acid sequences of TyrRSs from different organisms, using the PILEUP program (Needleman and Wunsch, *J. Mol. Biol.* 48:443–453 (1970)). From the aligned sequences, the "distances" between any two selected sequences, the evolutionarily conserved residues, and the average similarity among all members at each position were calculated, using the DISTANCE, the PRETTY and the PLOTSIMILARITY programs, respectively. These programs, designed by the Genetics Computer Group (Madison, Wis.), use the modified Dayhoff comparison table (Gribskov and Burgess, *Nucleic Acids Res.* 14:6745–6763 (1986)) for calculation.

The following sequences retrieved from GenBank were used in the multiple alignments of TyrRS amino acid sequences: *B. subtilis* (Grundy, F. J. and Henkin, T. M., *J. Bacteriol.* 172:6372–6379 (1990)), *B. stearothermophilus* (Bhat, T. N., et al., *J. Mol. Biol.* 158:699–709 (1982)), *B. caldotenax* (Jones, M. D., et al., *Biochemistry* 25:1887–1891 (1986)), *E. coli* (Barker, D. G., et al., *FEBS Lett.* 150:419–423 (1982)), *N. crassa* (Akins, R. A. and Lambiwitz, A. M., *Cell* 50:331–345 (1987)), *S. cerevisiae* (Henry, L., et al., *J. Biol. Chem.* 228:12855–12863 (1993)).

Several conserved regions were chosen for the design of degenerate oligonucleotides which were used to generate PCR fragments of the *Candida albicans* TyrRS gene. Sufficient sequence data was available so that degenerate primers could be designed for the specific amplification of either the cytoplasmic or the mitochondrial TyrRS genes from *C. albicans*. Table 1 shows the sequence of the degenerate oligonucleotide primers used for PCR amplification of the *C. albicans* tyrosyl-tRNA synthetase genes. KIYO-153 through KIYO-156 are also referred to herein as K-153 through K-156, respectively.

EXAMPLE 2

Cloning and Characterization of the PCR Products

The PCR products were visualized by UV fluorescence following electrophoresis on an agarose gel and staining with ethidium bromide. PCR fragments with the expected sizes were purified using a GeneClean II kit (Bio 101, LaJolla, Calif.), and ligated into pT7Blue T-vector (Novagen, Madison, Wis.). The ligation mixtures were used to transform *E. coli* DH5α competent cells which were then spread on LB agar plates containing 100 μg/ml ampicillin, 50 μg/ml X-Gal and 1 mM IPTG. White colonies were screened by direct colony PCR using vector specific reverse (U19) and forward (T7) primers to detect the presence and size of inserts. Colonies containing inserts of the expected size were used to inoculate 3 ml of LB containing 100 μg/ml ampicillin, and incubated at 37° C. overnight to produce cells for plasmid DNA isolation. Plasmid DNA was purified using the Wizard kit (Promega; Madison, Wis.), and the sequences of the inserts were determined by the dideoxy method using the USB Sequenase kit with 7-deazaG (7-deaza-2'-deoxyguanosine-5'-triphosphate labeling mix). Querying the sequences against the GenBank and the Swiss Protein Bank using the DNASTAR program and the BLAST program at the National Center for Biotechnology Information (NCBI), indicated that PCR fragments with sequences similar to either cytoplasmic or mitochondrial sequences of TyrRSs were obtained. The mitochondrial origin of the 420 bp PCR fragment (partial sequence in FIG. 1; SEQ ID NO:40) was concluded from the observation that its encoded amino acid sequence showed greatest homology to known bacterial tRNA synthetases or eukaryotic mitochondrial tRNA synthetases rather than to eukaryotic cytoplasmic enzymes. The most closely related sequence to the 420 bp fragment by the BLAST comparison program is that of the mitochondrial TyrRS gene of *S. cerevisiae*, which is 76% similar for the segment of DNA run in the query.

TABLE 1

Sequences of Degenerate PCR Primers Used for Amplification of
*C. albicans* Tyrosyl-tRNA Synthetases

| PRIMER NAME | SEQ ID NO: | PRIMER SEQUENCE (5' to 3') |
|---|---|---|
| KIYO-153 | 3 | ACI GGI TTR ATY GGI GAY CCH AGY GG |
| KIYO-154 | 4 | ACI GSI AAR ATY GGI GAY CCH ACH GG |
| KIYO-155 | 5 | ATR TTI CCC CAY TGR TCI GWI CCI CCR ATY T |
| KIYO-156 | 6 | ATR TTI CCR TAY TGR TCI GWI CCI CCR ATY T |
| R281 | 7 | TTG ATC WAC WCC AAA TTG ACA ATC |
| F100 | 8 | AAA YTW TAT TGG GGW ACW GCW CCW ACW GG |

R = A or G
Y = C or T
M = A or C
W = A or T
S = G or C
H = A, T or C
K = G or T
I = inosine Unless otherwise stated, when using degenerate oligonucleotides, each PCR amplification described in the exemplification was done in a 50 μl volume with 15 ng of *Candida albicans* genomic DNA from strain SC5314 (provided by Brendan Cormack, Stanford University), 100 pmoles of each primer, 1 mM Tris-HCl, pH 8.3, 150 μM MgCl$_2$, 5 mM KCl, 10 μg/ml gelatin, 50 μM of each dNTP, and 1.25 units of Taq DNA polymerase (Boehringer Mannheim). The reactions were performed in a PTC-100 thermal cycler (MJ research, Inc. Watertown, Mass.) for 30 cycles (94° C. for 30 seconds, 55° C. for 30 seconds, 72° C. for 70 seconds), followed by a 4 minute extension at 72° C.

TABLE 2

RESULTS OF PCR AMPLIFICATIONS USING COMBINATIONS OF
DEGENERATE PRIMERS DEFINED IN TABLE 1

| Primer Combination | Expected Size (bp) | PCR Product | Origin | Highest Similarity |
|---|---|---|---|---|
| K-153/K-155 | 420 | + | mitochondria | S. cerevisiae |
| K-153/K-156 | 420 | + | mitochondria | S. cerevisiae |
| K-154/K-155 | 420 | − | | |
| K-154/K-156 | 420 | − | | |
| R251/F100 | 543 | + | cytoplasm | S. cerevisiae |

EXAMPLE 3

Screening of C. albicans Genomic Libraries

A. Synthesis of specific DNA probes

From the information obtained by sequencing the PCR products of Example 2, specific oligonucleotide primers were designed (see Table 3) and used to generate a specific PCR fragment (PG-4.5), using C. albicans genomic DNA as template. Following purification with the GeneClean II kit (Bio 101), the PCR fragment was used as a template to generate radiolabeled probe DNA, by PCR or with the Random primed DNA labeling kit (Boehringer Mannheim), using [$^{32}$P]dCTP. The unincorporated nucleotides were removed by gel filtration using pre-packed Sephadex G-25 columns (Boehringer-Mannheim). These DNA probes were used in a Southern analysis to show that they hybridized to C. albicans DNA under high stringency conditions.

Figure 2A:
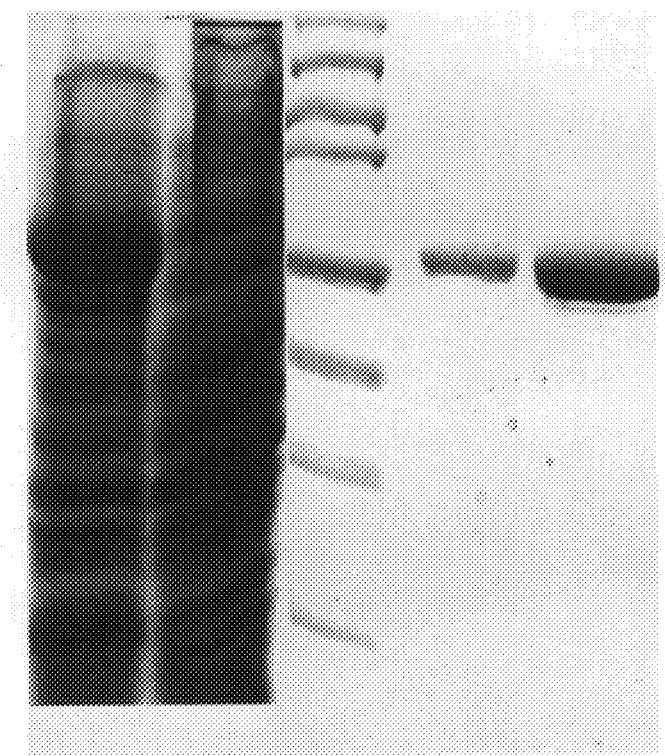
FIG. 2 is a photograph of an autoradiogram showing the result of hybridization of *C. albicans*-specific probe DNA (as obtained in Example 3A) with the Southern blot described in Example 3A. Loaded lanes on the gel were (1) λ HindIII-digested marker DNA; (2) DNA molecular weight marker X (Boehringer Mannheim); (3) 10 μg of EcoRI-digested rat DNA; (4) 2.5 μg of EcoRI-digested *S. cerevisiae* DNA; (5) 1 μg of EcoRI digested *E. coli* DNA; (6) 2.5 μg of EcoRI-digested *C. albicans* DNA; (7) λ HindIII-digested marker DNA; (8) DNA molecular weight marker X (Boehringer Mannheim).
Figure 2B:

The Southern blot was generated as follows. EcoRI digested rat (10 μg), yeast S. cerevisiae (2.5 μg), E. coli (1 μg), and C. albicans (2.5 μg) genomic DNAs were loaded onto a 0.8% agarose gel in TAE buffer and the gel was subjected to electrophoresis overnight. The gel was then briefly depurinated in 250 mM HCl, denatured in 0.5M NaOH/1.5M NaCl and neutralized in 1M Tris-HCl pH 7.4/1.5 M NaCl. The DNA was transferred onto a Gene-Screen plus nylon membrane (Dupont) overnight in 20× SSC (1×SSC is 150 mM NaCl, 15 mM Na-citrate, pH 7.0). Prehybridization and hybridization solutions consisted of 5× SSC/5× Denhardt's solution/0.5% SDS/5 mM EDTA, and 20 μg/ml of salmon sperm DNA. Each filter was incubated overnight at 65° C. with 10⁶ cpm of probe per ml of hybridization solution. The filters were then washed three times, for at least 30 minutes at 65° C., in 2× SSC/0.1 SDS. The Southern hybridization results were analyzed by autoradiography of the filter on X-ray film (Kodak X-OMAT). See FIG. 2.

TABLE 3

Oligonucleotide Primers Used for PCR Amplification of DNA Fragments for Use as Probes

| Oligonucleotide Sequence | SEQ ID | PCR Probe |
|---|---|---|
| PG-4: 5'-TCGTCTATAGCTTGCATCAATG-3' | 9 | PG-4.5 |
| PG-5: 5'-GAAGTCACAGTATTGTTGGC-3' | 10 | |

Note: PG-4 corresponds to nucleotides 660 to 639 of SEQ ID NO: 1 (coding strand) and PG-5 corresponds to nucleotides 341 to 360 of SEQ ID NO: 1 (non-coding strand).

B. Library screening

Two genomic C. albicans DNA libraries, constructed with DNA from strain WO-1 or with DNA from the highly pathogenic strain C9, were purchased from Dr. P. Magee (University of Minnesota). The Candida albicans strain C9 genomic library consists of Sau3A partial digest DNA fragments ligated into the BamHI site of the shuttle vector YPB (Goshorn, A., et al., Infect. Immun. 60:876–884 (1992), Goshorn, A. and Scherer, S., Genetics 123:667–673 (1989), Kwon-Chung, K. J., et al., Infect. Immun. 49:571–575 (1985)). The Candida albicans strain WO-1 pEMBLY23 library consists of HindIII and BamHI partial digest DNA fragments ligated into the BamHI site of the yeast shuttle vector pEMBLY23 (Slutsky, B. M., et al., J. Bacteriol 169:189 (1987); Baldari, C. and Cesareni, G., Gene 35:27 (1985)). The libraries were plated on 20×20 cm square LB+amp plates such that each plate contained 20,000 to 50,000 clones (6 to 10 genome equivalents) and incubated overnight at 37° C. Colonies were transferred to nylon membranes (GeneScreen Plus, Dupont). Each filter was successively transferred to solution I (10% SDS) for 3 minutes, then to solution II (0.5M NaOH/1.5M NaCl) for 5 minutes, and to solution III (1.5M NaCl/0.5M Tris-HCl pH 8.0) for 5 minutes for lysis, denaturation and neutralization, respectively. The filters were then air-dried, and baked in a vacuum oven at 80° C. for 2 to 3 hours. The filters were then prehybridized for several hours at 65° C. in hybridization solution (5× Denhardt's solution/5× SSC/0.5% SDS/10 mM EDTA and 20 μg/ml salmon sperm DNA) and hybridized overnight with probe PG-4.5 (see Table 3) as described in Example 3A. The filters were then washed three times at 65° C. with 2× SSC/0.1% SDS, and exposed to X-ray film at −80° C. to identify positive clones.

Positive clones were picked and resuspended in 1 ml of LB+amp medium. To obtain single colonies (200–500 per plate), various dilutions were plated on 150 mm diameter LB+amp plates and incubated overnight at 37° C. Colonies were transferred to Colony/Plaque Screen membranes and retested for hybridization to the probes as described above. Plasmids from single positive clones were isolated and digested with EcoRI (C9 library) or BamHI/HindIII (WO-1 library) restriction enzymes to determine the size of the inserts. The digested clones were also analyzed by Southern hybridization using the same DNA probes and hybridization conditions as for the library screening. Internal sequencing primers were used to sequence the cloned inserts to confirm that they contained motifs characteristic of TyrRS genes. The internal sequencing primers were designed based on sequence information obtained from the original TyrRS-specific PCR fragments (Table 2).

C. Results of library screen

Probe PG-4.5 (see Example 3A), specific for the cytoplasmic TyrRS gene, was used to screen the C9 C. albicans genomic library. EcoRI digestion of positive clones showed the presence of a uniform population having a single insert. After extensive screening of the library by hybridization and partial sequencing or PCR screening of all positive clones, all C. albicans TyrRS clones were found to be missing the first several amino acids of the protein, as indicated by sequence comparison to other known TyrRS genes and by the lack of an initiation codon. This may be due to the presence of a hypersensitive BamHI restriction site very close to the 5' end of the ORF. (The C9 library was constructed by partial Sau3A digest.) The same PG-4.5 probe was used to screen the WO-1 pEMBLY23 library. Fifty-nine positives were obtained following the first round of screening. However, partial characterization by restriction mapping, Southern analysis, PCR screening and sequencing showed that none of the new clones extended upstream of a BamHI site located within the 5' end of the gene. The missing 5' end of the gene was obtained by semi-specific PCR on genomic DNA using a specific internal primer directed toward the 5' end of the gene, and non-sequence specific primers chosen randomly from oligonucleotides available in the laboratory (See Example 4).

EXAMPLE 4

Cloning of the 5' End of the *Candida albicans* TyrRS Gene by Semi-Specific PCR

The 5' end of the *Candida albicans* TyrRS gene was obtained following three rounds of semi-specific PCR. Amplifications were done in a 50 µl reaction volume with 1x Taq polymerase buffer, 100 µM of each dNTP, 2.5 units of Taq DNA polymerase (Boehringer-Mannheim) with the indicated amount of template DNA and primers.

First PCR

Each tube contained 50 ng of *Candida albicans* genomic DNA, 10 pmole of specific primer PG11, and 20 pmole of one non-specific primer (see Table 4); 10 different non-specific primers were tested in combination with PG11. PCR conditions were as follows. After an initial incubation at 94° C. for 2 minutes, PCR products were generated in 30 successive cycles at 94° C. (30 seconds), 50° C. (30 seconds) and 72° C. (40 seconds), followed by a final extension step at 72° C. for 2 minutes. The PCR products were purified with the Wizard PCR Preparation Purification System Reagents (Promega) and resuspended in 50 µl $H_2O$. Seven of the PCR products were sequenced using the fmol DNA Sequencing System kit (Promega) and Ca-tyr-01 specific primer. Sequencing results suggested that 4 of the PCR reactions yielded *Candida albicans* TyrRS-specific DNA. Results are summarized in Table 4.

Second PCR

1 µl of each of the 4 PCR products having TyrRS-specific sequences was used as a template for unidirectional amplification with 40 pmol of Ca-tyr-01 primer, to enrich the upstream sequence from each primer. The PCR products were generated by 30 cycles at 94° C. (30 seconds), 60° C. (30 seconds) and 72° C. (40 seconds), followed by a final extension at 72° C. for 2 minutes.

Third PCR

1 µl of each of the 4 PCR products from the second round of PCR reactions was used as a template for amplification with 40 pmol of Ca-tyr-01 primer and 20 pmol of the non-specific primers used in the first PCR reaction (see Table 4). The PCR products were generated by 30 cycles at 94° C. (30 seconds), 50° C. (30 seconds), 72° C. (40 seconds), followed by a final extension at 72° C. for 2 minutes.

Bands in a sample of the third PCR were separated by electrophoresis on a 1% agarose gel. Multiple bands from each reaction were visible by uv-illumination of the ethidium bromide-stained gel. Each PCR was processed with the Wizard PCR Preparation Purification System Reagents (Promega) and sequenced with a specific internal primer (Ca-tyr-03) using the fmol PCR sequencing system (Promega). The recommended protocol was used, except that annealing was done at a slightly higher temperature (50° C. for 30 seconds, instead of 42° C. for 30 seconds). All four sequencing reactions yielded sequences containing the 5'end of the *Candida albicans* TyrRS gene. The new sequence information adds the missing N-terminal amino acid residues (MTVIT) to the sequence obtained from genomic clones.

EXAMPLE 5

Nucleotide and Deduced Amino Acid Sequence of the *Candida albicans* TyrRS Gene

Sequencing was done directly on the purified positive plasmid clones pG42 (also called $pC^3607$; preserved in *E. coli* host JM109) and pG43 (also called $pC^3608$; preserved

TABLE 4

Sequence of PCR Primers Used for Cloning 5' End of Candida TyrRS Gene and Results of First Round of Non-specific PCR

| Specific Primer | Seq. ID NO: | Primer Sequence | | |
|---|---|---|---|---|
| PG-11 | 11 | 5'-GCCAACAATACTGTGACTTC-3' | | |
| Ca-tyr-01 | 12 | 5'-CTATTTTCTTTTTCTAGAACATC-3' | | |
| Ca-tyr-03 | 13 | 5'-CTTTAATGATTTGCCCATTGAGAG-3' | | |

| Non-specific Primer | Seq. ID NO: | Primer Sequence | PCR Product | TyrRS-Specific |
|---|---|---|---|---|
| Met JT14 | 14 | 5'-TATGCAATTGCATTTTAGGCAC-3' | + | |
| Met JT16 | 15 | 5'-ACT CAT TTT CAC GCC CTC TAT C-3' | + | + |
| Lys JT1 | 16 | 5'-TTGATTGTAGGGGGGTTTGAAGC-3' | + | |
| Lys JT2 | 17 | 5'-CTTGCGTTCGCCCCGCCAGG-3' | + | |
| Lys JT3 | 18 | 5'-GTA GAG CAT CAA CTC ATT AAC CCAC-3' | + | + |
| Lys JT4 | 19 | 5'-AAACATAGGCTTGCAAAATCGCGCT-3' | − | |
| Lys JT5 | 20 | 5'-CCAATACATGGATGAAGATTAC-3' | − | |
| Lys JT12 | 21 | 5'-ATACCCTTACTAATGCCCCCTATCG-3' | − | |
| Ile JT1 | 22 | 5'-GATAGTGGTAGCACCTTTAAGGCGG-3' | + | + |
| Ile JT2 | 23 | 5'-TAA TCG CTC TAA AAT TTG CTG CTC-3' | + | + | in *E. coli* host JM109) using oligonucleotide primers specific to the internal sequences of the genes to extend toward the 5' and 3' end of the gene within the insert. For *Candida albicans* cytoplasmic TyrRS, the sequence within the ORF was determined for both DNA strands. The individual sequences obtained at each round of sequencing were assembled using the DNA Sequence Management Program of the DNASTAR package to generate contiguous sequences. The methionine initiation codon was identified by comparison with sequences of corresponding TyrRSs present in GenBank using the Multiple Sequence Alignment program (DNASTAR; Madison, Wis.).

The 1430 basepair sequence containing the *C. albicans* cytoplasmic tyrosyl-tRNA synthetase gene is shown in FIGS. 3A–3B (SEQ ID NO:1). The open reading frame (ORF) is 1227 basepairs and encodes a polypeptide of 409 amino acids, with translation starting at the ATG at position 134. SEQ ID NO:2 is the polypeptide translated form the ORF by the universal genetic code. The deduced amino acid sequence contains class defining motifs ($^{51}$HCGY$^{54}$ and $^{225}$KMSAS$^{239}$). The cysteine residue in the $^{51}$HCGY$^{54}$ is extremely rare among class I synthetases and has only been found in the TyrRS of fungal organisms. The cysteine residue in HCGY is present not only in the TyrRS of *Candida albicans*, but also in the TyrRSs of *S. cerevisiae* and *Pneumocystis carinii*. There is a valine residue at this position in the human homolog. Similarly, the alanine residue (A) in the KMSAS motif might be specific to fungi. It is also found in *P. carinii* and *S. cerevisiae* but not in *H. sapiens*, where a serine residue is found at the corresponding position.

As expected from the initial results of the library screening, there is a BamHI restriction site in the open reading frame from bases +15 to +20 (148–153 in SEQ ID NO:1) in the codons for amino acids 5 through 7.

*Candida albicans* uses a non-universal genetic code; the codon CUG, which normally codes for leucine in most organisms, including *S. cerevisiae*, codes for serine in several species of Candida (Ohama, T., et al., *Nucleic Acids Res.* 17:4039–4046 (1993)). There is one CUG codon in the *Candida albicans* TyrRS ORF, which corresponds to amino acid residue 323 in the polypeptide. When the *C. albicans* TyrRS gene is expressed in *S. cerevisiae* or in other organisms which use the universal genetic code, the CUG is expected to encode leucine in the expressed recombinant protein. When the *C. albicans* TyrRS gene is expressed in *C. albicans* or in other species of Candida which use nonuniversal decoding, the expected amino acid residue at position 323 is serine, as in SEQ ID NO:39. Residue 323 is located in a non-conserved region of the protein.

The *C. albicans* TyrRS amino acid sequence was compared with the TyrRS sequences available in the databank by using the Multiple Sequence Alignment Program from the DNASTAR package. Percent similarity and percent divergence among these sequences were determined using the Clustal method with PAM250 residue weight table. The percent similarity between the predicted amino acid sequence of the *C. albicans* cytoplasmic TyrRS and the protein identified as cytoplasmic TyrRS from *S. cerevisiae* was found to be 69%. At the DNA level, the ORFs of the *Candida* albicans and *S. cerevisiae* cytoplasmic TyrRS genes were found to share 63% identity. Other sequences were less related.

EXAMPLE 6

Expression of *C. albicans* Tyrosyl-tRNA Synthetases as N-terminal GST-Fusion Proteins The TyrRS gene was fully sequenced and several constructs for expression and purification of the protein were made in *E. coli* using the pGEX-4T-2 expression vector (Pharmacia) that allows construction of a gene encoding an N-terminal GST-fusion protein. Plasmid pG42 expresses a GST-TyrRS fusion protein missing the N-terminal 5 amino acids of the wild type TyrRS protein. Plasmid pG43 expresses a hybrid GST-TyrRS fusion protein in which the missing 5 aminoterminal amino acids of *C. albicans* TyrRS were replaced by the first 7 amino acids of the S. cerevisiae TyrRS. A third construct, pC$^3$695, that contains the entire open reading frame of the *Candida albicans* TyrRS gene, was also made and transformed into *E. coli* strain BL21.
Expression constructs To make plasmids pG42 and pG43, the following oligonucleotide primers were synthesized and used for PCR amplification of the TyrRS gene from *C. albicans* DNA.

PG-42 5' primer (SEQ ID NO:24):
    5'-CGC<u>GGATCC</u>GATCCAGTTGAACAATATAA-
        TTTAATTACC-3'

PG-43 5' primer, introduces 5' end of *S. cerevisiae* TyrRS gene (SEQ ID NO:25):
    5'-CGC<u>GGATCC</u>ATGTCCTCTGCTGCCACGG-
        TTGATCCAGTTGAACAATATAATTTAATTA-
        CC-3'

PG-44 3' primer (SEQ ID NO:26):
    5'-CCG<u>CTCGAG</u>CGGTACAAATTATTCAGTAG-
        TTGGTAACTCATG-3'

The 5' oligonucleotide primers contained a BamHI restriction site (underlined). For PG-43, the BamHI restriction site is immediately upstream from the ATG initiation codon (in bold). The 3' oligonucleotide primer contained an XhoI restriction site (underlined) and the stop codon (in bold, TAA in the coding strand).

PCRs were done in 50 μl volumes with 2.5 units of Vent polymerase (New England Biolabs; Beverly, Mass.), 50 μM dNTPs, 2 to 10 mM MgSO$_4$, 50 pmole of each primer (pairs tested were pG42 5' primer+pG44 3'primer; pG43 5' primer+ pG44 3' primer). The reactions were first incubated for two minutes at 94° C., followed by 20 cycles at 94° C. (40 seconds), 55° C. (30 seconds) and 72° C. (150 seconds). The template DNA was the C9 genomic library plasmid pC$^3$602 (also called TyrGA6). A 1:100 dilution of mini-prep DNA (~50 ng) was used per PCR.

Although PG-44 is not an exact match of the non-coding strand of the 3' end of the TyrRS gene (nucleotides 34–42 of SEQ ID NO:26 from the TyrRS gene), PCR using the PG-44 and PG-43 primers on the C9 genomic library plasmid pC$^3$602 as template yielded a band of the expected size. The PCR product was sequenced directly and found to have the same 3' end as the TyrRS gene found in pC$^{3607}$ and pC$^3$608.

The 1.8 kb PCR products were purified (Wizard kit; Promega, Madison, Wis.), digested with BamHI and XhoI restriction enzymes, purified (GeneClean II) and ligated into BamHI/XhoI digested pGEX-4T-2 expression vector. Both the pG42 and pG43 plasmids put the *C. albicans* TyrRS gene under the control of the Tac promoter. The ligation mixtures were used to transform electro-competent *E. coli* JM109 cells. (Attempts to produce the *C. albicans* TyrRS gene in *E. coli* strain DH5α failed because of poor expression and insolubility problems.) Single colonies from each transformation were transferred to LB+amp and incubated at 37° C. overnight. The overnight cultures were used to inoculate fresh LB+amp medium which was incubated at 37° C. until the cultures reached an OD$_{600}$ of 0.7 to 1. IPTG was added to a final concentration of 1 mM and the cells were shifted to 18° C. for 3 days, harvested by centrifugation, then lysed by one passage through a French press. The clarified cell extracts, obtained by centrifugation of the cell lysates for 30 minutes at 13,000 rpm (Sorvall), were tested for tyrosyl-tRNA synthetase activity (see Example 7B). An extract of cells containing pGEX-4T-2 was used as a control. The fusion proteins were purified by affinity chromatography as described in Example 7A and their activities were characterized.

To make pC³695, the following two primers were used to amplify by PCR the 5' end of the ORF of the C. albicans TyrRS gene.

Ca-Tyr-04 (SEQ ID NO:27):
5'-CGC<u>GGATCC</u>TATGACAGTCATAACAGATCC-AGTTGAACAATAT-3'

Ca-Tyr-O1 (SEQ ID NO:12):
5'-CTATTTTTCTTTTTCTAGAACATC-3'

Ca-Tyr-04 is the 5' end primer with a BamHI cloning site (underlined) upstream from the ATG and a silent mutation G15A (in bold) to destroy the endogenous BamHI site which is found within the codons for amino acid residues 5 through 7. Ca-Tyr-O1 is complementary to the C. albicans TyrRS gene 80 bases downstream of Ca-Tyr-04.

PCR amplifications were done with 100 µM of each dNTP, 2.5 units Taq polymerase, 100 ng of Candida albicans genomic DNA, 120 ng of each primer for 30 cycles at 94° C. (30 seconds), 55° C. (30 seconds), and 72° C. (40 seconds), followed by a 2 minute extension at 72° C. PCR products were purified (Wizard purification kit; Promega) and digested with BamHI and XbaI restriction enzymes. The digested PCR fragments were isolated on a 1% agarose gel, purified (GeneClean II) and ligated into BamHI/XbaI-digested pG42 or pG43 plasmids. The expression constructs were used to transform E. coli DH5α competent cells. Transformants containing the correct constructs were identified by colony PCR, and their plasmid DNA isolated and sequenced for confirmation that the expected ORF sequence was present.

EXAMPLE 7

Purification and Enzymatic Characterization of Fusion Proteins

A. Purification

For protein production and purification, the expression construct pC³695 was introduced into E. coli strain BL21. Cells were grown in LB+amp at 37° C. until late log phase and expression was induced by the addition of IPTG to 0.1 mM. Cells were harvested 4 hours after IPTG induction and kept at −20° C. until lysis. Cells were resuspended in cold PBS buffer containing 5 to 10 mM DTT, 100 µg/ml lysozyme, 1 mM phenylmethylsulfonyl fluoride (PMSF) and other protease inhibitors (5 µg/ml each of leupeptin, pepstatin, chymostatin and papain), and lysed by passage through a French pressured cell. Triton X-100 may be added to a final concentration of 1%.

Figure 4:
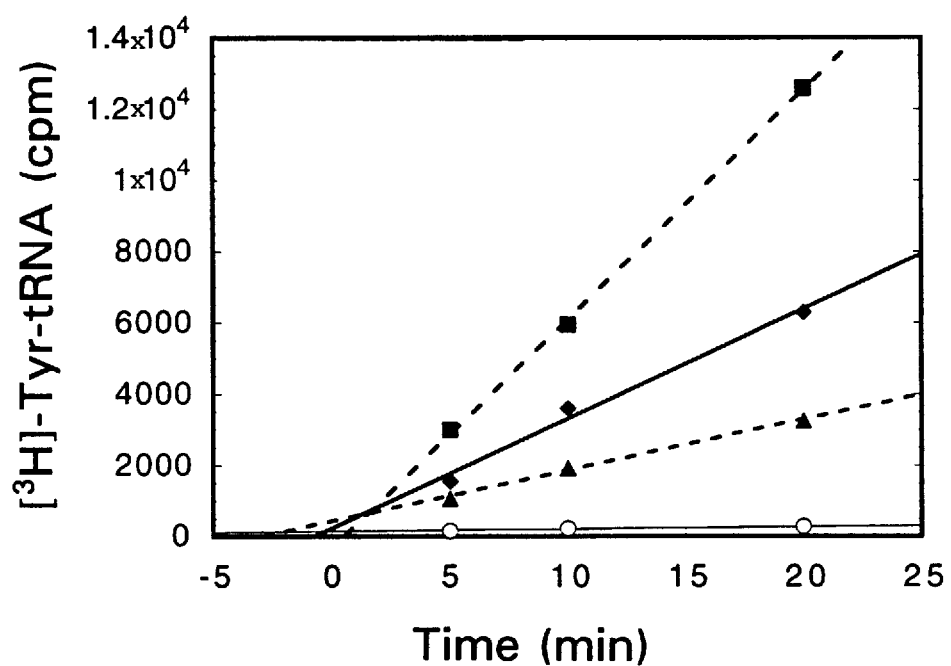
FIGS. 4A–4B consist of two photographs of Coomassie blue-stained SDS-polyacrylamide gels.

Following cell lysis, whole cell extracts of BL21(pC³695) were clarified by centrifugation at 20,000×g for 15 minutes at 4° C., and clarified cell extracts were tested for TyrRS activity. A cell extract of BL21(pGEX-4T-2) was used as a negative control. GST-fusion proteins were purified by affinity chromatography on Glutathione-Sepharose 4B (Pharmacia) equilibrated with PBS. Cell extracts were filtered through a 0.45 µm filter (Nalgene) and either mixed with the resin in batch or loaded onto a column containing the resin. Unbound proteins were washed off the resin with ice cold PBS (10 bed volumes) and bound proteins were eluted off the resin in 3 bed volumes of PBS containing 10 mM glutathione, then concentrated by ultrafiltration using centrifuge concentrators (Centiprep 30 or Centricon 30; Amicon), and stored at pH 7.5 at 20° C. in 40% glycerol in the presence of 5 to 20 mM DTT. The GST moiety was removed following incubation of the purified proteins with 0.5 unit thrombin at 16° C. for 16 hours. Proteins were visualized on a 10% SDS-polyacrylamide gel following staining with Coomassie blue (FIGS. 4A–4B). The purity of the GST-fusion protein produced in BL21(pC³695) is estimated to be at least about 85%. Affinity-purified fusion protein produced in JM109(pG42) and JM109(pG43) appeared on SDS-polyacrylamide gels as a doublet of approximately 60 kD.

B. Enzymatic activity

The purified recombinant GST-fusion proteins and thrombin-cleaved proteins of C. albicans TyrRS were tested for their charging activities. Charging assays were based on the procedure of Shepard et al. (Proc. Natl. Acad. Sci. USA 89:9964–68 (1992)). A typical 50 µl reaction was carried out at 25° C. and contained 4 mM ATP, 20 µM of tritium-labeled amino acid, 90 µM crude tRNA from E. coli (Sigma) or brewer's yeast (Boehringer Mannheim), 10 µM KF, 50 mM HEPES, pH 7.5, 10 mM MgCl$_2$, 10 mM DTT or β-mercaptoethanol and 20 mM KCl. Purified enzyme was diluted in 100 mM HEPES, pH 7.5, 20 mM DTT and 0.1 mg/ml BSA.

Figure 5:
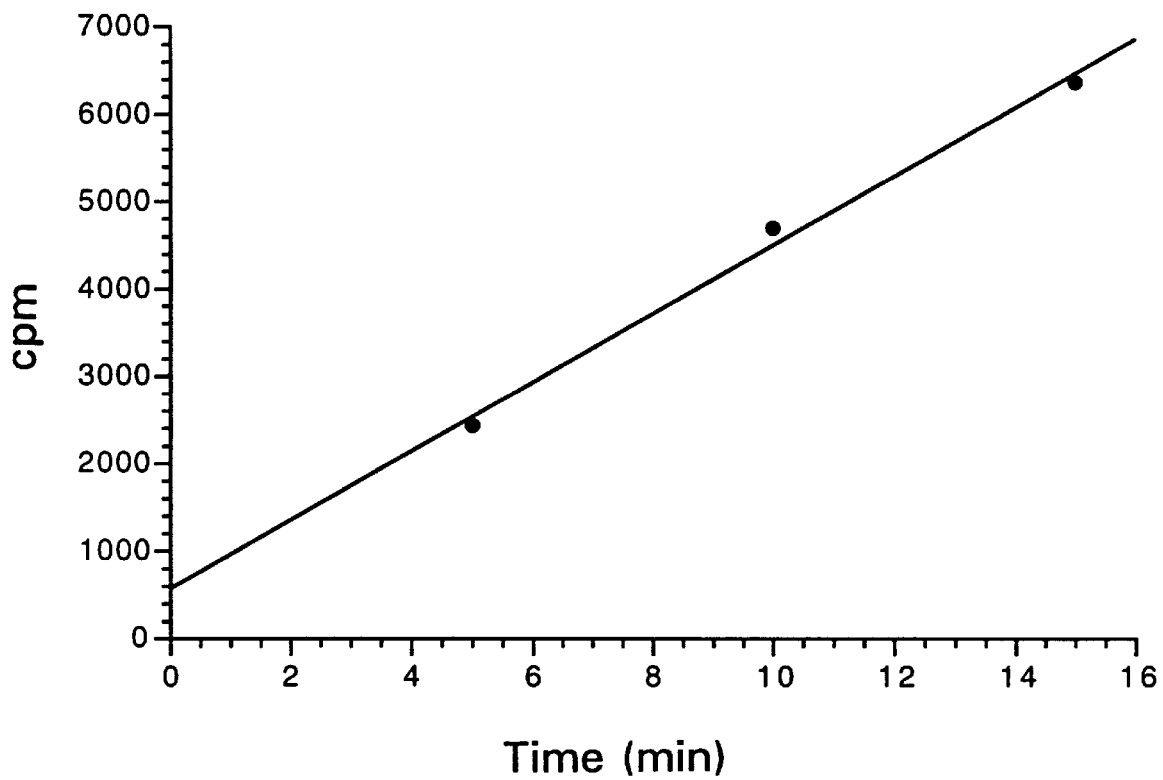
FIG. 5 is a graph illustrating the aminoacylation activity (cpm, counts per minute of [$^3$H]tyrosyl-tRNA) over time (minutes) of the purified N-terminal GST-TyrRS (28 nM) expressed from plasmid pG43, using crude total tRNA from *E. coli* (□), crude total tRNA from brewer's yeast (■), or no tRNA (▲). (See Example 7B.)

Reactions were started by the addition of enzyme to the reaction mix preincubated at 25° C. At various time intervals, 10 µl of the reaction mix was spotted on 3 MM Whatman filter circles which were then immersed into ice cold 5% trichloroacetic acid (TCA). After three washes in ice cold 5% TCA (at least 15 minutes each), the filters were rinsed once with cold ethanol, once with ether, and air dried. The radioactivity was quantitated by counting the pads in a table top scintillation counter (Packard) in the presence of scintillation fluid (Betafluor; National Diagnostics). See FIG. 5 and FIG. 6.

For determination of $K_m$, various concentrations of one substrate (ATP, amino acid, or tRNA) were used while the other two substrates were kept at saturating concentrations. To test the effect of temperature, the reactions were incubated at 25°, 30°, 37° and 42° C. The Bradford assay was used for determination of total protein. The proportion of active enzyme was calculated by monitoring the formation of the amino acid-adenylate:enzyme complex using a nitrocellulose filter binding assay in the presence of various dilutions of enzyme preparation. A 50 µl reaction contained 1 mM ATP, 1 unit of pyrophosphatase, 50 mM Tris-HCl, pH 5.8, 10 mM MgCl$_2$, 30 mM KCl, 20 mM DTT, 40 µM of labeled tyrosine, and diluted enzyme.

All three expression constructs produced active GST-TyrRS enzyme. The apparent molecular weights of the fusion proteins were around 70 kD. The various purified Candida albicans GST-TyrRSs charged S. cerevisiae crude tRNAs efficiently, but not E. coli tRNAs. About 25 nM purified enzyme was used in a standard charging assay. $K_m$ for tyrosine was measured for all three fusion enzymes and found to be 8 to 10 µM. To determine $K_m$, the amino acid concentration was varied from 0.625 µM to 50 µM. The GST-fusion protein containing the full-length Candida albicans TyrRS polypeptide was chosen for further kinetic studies. Optimum activity was obtained with 5 mM MgCl$_2$, 4 mM ATP and 150 mM KCl. $K_m$ was approximately 0.5 mM for ATP (concentration range from 0.025 to 10 mM), 14.4 µM for tRNA (0 to 200 µM) and 8 to 10 µM for tyrosine (0.625 to 50 µM).

The GST moiety was removed efficiently following thrombin cleavage. Activity of the cleaved protein increased 3-fold. This may be due to the fact that tyrosyl-tRNA synthetases function as dimers and that the GST moiety might decrease the stability of the homodimer.

EXAMPLE 8

Genetic Complementation of S. cerevisiae Tyrosyl-tRNA Synthetase Null Mutants

The ability of the C. albicans tyrosyl-tRNA synthetase gene to complement a Saccharomyces cerevisiae tyrosyltRNA synthetase null strain was tested. For complementation assays, S. cerevisiae TyrRS null strains (QBY374 and QBY375) were constructed (see below for details) The haploid null strains contain a deletion of the TyrRS gene and a maintenance plasmid (pC$^3$679) with a URA3 selectable marker, which provides wild type TyrRS activity in trans.

The Candida albicans TyrRS gene was cloned into a Saccharomyces cerevisiae expression vector (pQB169) that contains a LEU2 selectable marker, to yield plasmids pC$^3$771 and pC$^3$772, both derived from the fusion gene in pG42, and plasmids pC$^3$773 and pC$^3$774, both derived from the fusion gene in pG43. For complementation assays, the S. cerevisiae null strain was transformed with pC$^3$771, pC$^3$772, pC$^3$773 or pC$^3$774, and transformants were selected on minimal plates lacking leucine (SC-Leu). Transformants were then replated on media containing 5-FOA to select against cells containing the URA3 maintenance plasmid bearing the wild type S. cerevisiae TyrRS gene. Survival of cells on 5-FOA-containing media demonstrates that the Candida albicans TyrRS gene can provide the sole source of tyrosyl-tRNA synthetase enzymatic activity and thus can fully substitute for the S. cerevisiae enzyme in vivo.

Construction of Saccharomyces cerevisiae null strain for TyrRS gene: Construction of maintenance plasmid pC$^3$679

Plasmid p13Gen containing the S. cerevisiae TyrRS gene was obtained from Professor U. Rajbhandary (MIT, Chow, M. C. and Rajbhandary, U. L., J. Biol. Chem. 268:12855–12863 (1993)). p13Gen is a genomic DNA clone of the yeast cytoplasmic TyrRS gene isolated from a Saccharomyces cerevisiae genomic DNA library. The library was made in the vector pCT3, by Craig Thompson in the laboratory of R. Young at the Whitehead Institute. The ORF of the gene and its upstream 5' end containing the promoter was obtained by PCR, using conditions as follows: 95° C. (2 min), 30 cycles of 95° C. (30 seconds), 55° C. (30 seconds), 72° C. (1 min), followed by a 5 minute extension at 72° C. The following PCR primers were used:

YYRSN1 (SEQ ID NO:28): 5'-GAATTCCATATGGA-CAAGAGATCCCCTGCTGTTGTCTCC-3'

YYRSN6 (SEQ ID NO: 29 ): 5'-GATCCCGGGGAAT-CGTGAAAACGGATTAAGCTATGC-3'

Primer YYRSN1 was designed to match the coding strand of a region approximately 420 basepairs 5' of the initiaion site of the S. cerevisiae cytoplasmic TyrRS gene.

Primer YYRSN6 contains a XmaI restriction site (underlined) at its 5' end; the sequence at the 3' end is that of the non-coding strand immediately downstream of the S. cerevisiae TyrRS ORF.

The 1.6 kb PCR product was purified with the GeneClean kit (Bio 101, LaJolla, Calif.), directly ligated into pT7Blue T-Vector (Novagen), and the ligation mixture was used to transform E. coli DH5α cells, which were plated on LB+amp indicator plates containing X-Gal. White transformant colonies were screened for insert size and orientation by PCR, using the YYRSN6 and T7 primers. DNA from colonies that gave PCR products of 1.6 kb was isolated, digested with SphI and XmaI restriction enzymes (which do not cut within the TyrRS gene), and gel purified. Vector pQB173, a CEN plasmid with a selectable URA3 marker, was also digested with SphI/XmaI restriction enzymes. The vector backbone fragment was purified following separation of fragments by gel electrophoresis. The vector backbone, which does not contain the ADH promoter, was ligated to the 1.6 kb fragment, yielding plasmid pC$^3$679. The ligation mixture was used to transform E. coli DH5α cells, which were spread on LB+amp plates and incubated overnight at 37° C. Transformants were screened by colony PCR with the YYRSN1 and YYRSN6 primers. Plasmid DNA was isolated from positive clones.

Construction of the null strain

The 3' and 5' non-coding flanking regions of the S. cerevisiae TyrRS gene were recovered by PCR as described above, using plasmid p13Gen as DNA template. The 462 bp 3' flanking region which includes the last 43 bp of the ORF and extends 419 bp past the stop codon was obtained with the primer combination YYRSN4/YYRSN3. The 398 bp 5' flanking region, which ends 6 bases before the initiation codon, was obtained using the primer combination YYRSN1/YYRSN2. The sequences of the primers are below:

YYRSN2 (SEQ ID NO:30): 5'-CGCGGATCCCGTCAATTAGAGTATGCGGTTA-TGGATG-3'

YYRSN3 (SEQ ID NO:31): 5'-CGCGGATTCGACCAACGAGATTGCCACGA-AACTAGAGG-3'

YYRSN4 (SEQ ID NO:32): 5'-CGGGGTACCGAAGGAGGGGCAAAGAAAG-CAGGATGC-3'

The 5' flanking region was isolated by gel electrophoresis, purified with the GeneClean kit and digested with KpnI and NdeI restriction enzymes. The 3' flanking region was treated as above but digested with KpnI and BamHI restriction enzymes. The digested DNAs were purified using the GeneClean kit. pT7Blue T-Vector was digested with NdeI and KpnI restriction enzymes, purified using the GeneClean kit, and ligated to the digested, purified 3' and 5' flanking regions, to yield plasmid pQB682 (or pYYRSNS1). The ligation mixture was used to transform E. coli DH5α cells, which were then plated on LB+amp plates. Transformants were screened by colony PCR using primers YYRSN4 and YYRSN1. Plasmid DNA was isolated from colonies that showed the expected 800 bp PCR fragment.

S. cerevisiae TRP1 was obtained by digestion of plasmid pQB29 with BamHI restriction enzyme, followed by gel purification (pQB29 =YDp-W described in Berben, G. et al., Yeast 7:475–477 (1991)). Plasmid pQB682 was digested with BamHI, then treated with phosphatase for 30 minutes at 37° C. and purified by gel electrophoresis. The BamHI TRP1 DNA fragment from pQB29 was ligated to BamHI-digested pQB682 to yield plasmid pYYl which contains TRP1 inserted between the 5' and 3' flanking sequences for the S. cerevisiae TyrRS gene. DH5α cells were transformed with the ligation mixture and spread on LB+amp plates. Transformants were screened by colony PCR using primers YYRSN1 and YYRSN4. Plasmid DNA was isolated from the correct clones that gave a PCR product of 2 kb. To delete the chromosomal TyrRS gene and replace it with an insertion of TRP1, S. cerevisiae strain Y93 (also called FY83;MATa/α lys2-128δ/lys2-128δleu2Δ1/leu2Δ1 ura3-52/ura3-52 trp1Δ63/trp1Δ63, obtained from Fred Winston of Harvard Medical School), was transformed with plasmid pYY1 linearized with KpnI restriction enzyme, and transformants were selected for a Trp+phenotype. The presence of a deletion in the TyrRS gene was confirmed by PCR using primers YYRSN1 (above) and YYRSN7 (5'-CATCAGCAACGGACATATTGG-3'; SEQ ID NO:33). Two PCR bands of 2189 and 1822 bp were observed, indicating that one of the copies of the TyrRS gene had been replaced by TRP1. This heterologous diploid strain was designated QBY376. To generate haploid strains QBY374 and QBY375, the diploid strain was first transformed with the maintenance plasmid (pC$^3$679), then set for sporulation and tetrad dissection.

Construction of yeast expression vectors pQB169 and pQB172

Plasmid pMC4 carries the ADH promoter of *S. cerevisiae*, and downstream of the promoter, the coding sequence for the cytochrome oxidase IV mitochondrial targeting peptide (Pinkham, J., et al., *Mol. Cell. Biol.* 14:4643–4652, (1994); Hurt, E. C., et al., *J. Biol. Chem.* 262:1420–1424 (1987); Hurt, E. C., et al., *EMBO J.* 3:3149–3156 (1984)). Derivatives of plasmid pMC4 can be constructed which lack a functional mitochondrial targeting sequence to allow cytoplasmic expression. Alternatively, the ADH promoter of pMC4 can be excised and inserted into another suitable vector. Plasmids pQB169 and pQB172, which were constructed for the expression of heterologous genes in yeast cytoplasm, are examples of vectors constructed in this manner. pQB169 contains the constitutive ADH promoter, a polylinker and the ILS1 transcriptional terminator. A 450 bp fragment containing the constitutive ADH promoter (pADH) with its transcriptional start sites (but not a translational start site (i.e., ATG)) was amplified by PCR using plasmid pMC4 as template. Primers were designed to incorporate a HindIII restriction site (in bold below) at the 5' end (primer JK-1, SEQ ID NO:34) of the fragment and a PstI restriction site (in bold below) at the 3' end (primer JK-2, SEQ ID NO:35):

JK-1 (SEQ ID NO:34):
5'-CCAAGAAGCTTGAAGTAATAATAGGCGCAT-GC-3'

JK-2 (SEQ ID NO:35):
5'-CGTACTGCAGGATTGTATGCTTGGTATAGC-3'

The resulting PCR product was cleaved with HindIII and PstI restriction enzymes, and the HindIII-PstI fragment containing pADH was subcloned into the HindIII and PstI restriction sites of vector YEplac181 (Gietz and Sugino, *Gene* 74: 527–534 (1988)), a 2μ LEU2 yeast shuttle vector, to yield intermediate plasmid pQB147.

For efficient transcription termination, a 270 bp terminator fragment (tILS1), containing conserved transcription termination signals (Zaret, K. S. and F. Sherman, *Cell* 28: 563–573 (1982)) was generated by PCR, using plasmid pQB89 as template.

The 270 bp tILS1 PCR fragment was engineered to have an EcoRI restriction site (in bold below) at the 5' end (JK-5, SEQ ID NO:36), and a NarI restriction site (in bold below) at the 3' end (JK-6, SEQ ID NO:37), and contains the 3' untranslated region of ILS1, including bases 3519–3846 of the ILS1 gene. The primers used to prepare this fragment were:

JK-5 (SEQ ID NO:36):
5'-GGA ATT CTG AAA ACA ACT CAT ATA AAT ACG-3'

JK-6 (SEQ ID NO:37):
5'-GAG GCG CCC TCT TAT CAA TCC CCT CCT CAA CC-3'

The resulting PCR product was cleaved with EcoRI and NarI restriction enzymes. pQB147 was cleaved with EcoRI and NarI, and the EcoRI-NarI tILS1 fragment was subcloned into the EcoRI and NarI restriction sites of the vector, to yield expression vector pQB169. Transformants of *E. coli* DH5α containing pQB169 were obtained. Transcription of a gene inserted into this vector can be initiated from pADH, and translation can be initiated at the first ATG of the insert.

To make a single-copy (CEN) version of this vector, the expression cassette (pADH-polylinker-tILS1) of pQB169 was excised with HindIII and NarI, and was subcloned into the HindIII and NarI restriction sites of HindIII-NarI cut YCplac111 (Gietz and Sugino, Gene 74:527–534 (1988)) to yield pQB172. Transformants of *E. coli* DH5α containing pQB172 were obtained.

Construction of pC³771. pC³772. pC³773 and pC³774. and complementation results

Four plasmids (*S. cerevisiae* shuttle vectors pC³771 and pC³772 derived from pG42; and shuttle vectors pC³773 and pC³774 derived from pG43), expressing either the hybrid *Candida albicans* tyrosyl-tRNA synthetase gene (derived from *E. coli* expression plasmid pG43) or the N-terminal truncation (derived from *E. coli* expression plasmid pG42) were constructed to test for complementation in the *S. cerevisiae* null strain QBY374. The coding regions within pG43 and pG42 were recovered by PCR (35 cycles at 94° C. (30 seconds), 55° C. (30 seconds), 72° C. (25 seconds) followed by a 2.5 minute extension at 72° C.) using plasmids pG42 or pG43 as DNA template. The PG-43 and PG-42 primers were used as 5' primers and a new primer (CA-tyr-3', SEQ ID NO:38) was designed to match the 3' end of the *C. albicans* TyrRS gene. Ca-tyr-3' also introduces a KpnI restriction site (underlined in sequence below).

CA-tyr-3' (SEQ ID NO:38):
5'-AAGGGGTACCCCTTATTCAGTAGTTGGCTT-TTC-3'

PCR amplification was done with 50 μM of each dNTP, 1× Vent polymerase buffer (New England Biolabs), 2 mM MgSO₄, 2 units of Vent DNA polymerase (New England Biolabs), 200 ng of plasmid DNA and 100 pmol of each primer. PCR products were purified with the Wizard purification kit (Promega), digested with BamHI and KpnI restriction enzymes, purified using the GeneClean kit, and ligated into BamHI/KpnII digested pQB169. Positive plasmids 169-Ca-tyr-42 (pC³771 and pC³772) and 169-Ca-tyr-43 (pC³773 and pC³774)(DH5α transformants) were identified, their DNA isolated, and the recombinant plasmids were transformed into the yeast tester strain QBY374. The *C. albicans* TyrRS hybrid gene expressed from plasmid 169-Ca-tyr-43 was found to rescue the null phenotype as demonstrated by the ability of the cells containing the plasmid to grow on 5-FOA containing medium. As expected, the truncated gene expressed from plasmid 169-Ca-tyr-42 was unable to complement, since the coding region did not start with an ATG. pC³771, pC³772, pC³773 and pC³774 were transformed into strain QBY329 and selected on SC-Leu plates. Four colonies from transformation plates with pC³771, pC³772 and pC³773, and one colony from transformation plates with pC³774 were tested by replica plating droplets of cell suspensions onto both SC-Leu and SC+5-FOA plates. Four out of the 5 colonies tested from cells carrying pC³773 and pC³774 grew on 5-FOA medium. Transformants of pC³771 and pC³772 did not grow on 5-FOA.

EXAMPLE 9

Aminoacylation Activity of TyrRS Isolated from *C. albicans*

For *C. albicans* tyrosyl-tRNA synthetase, the kinetic values of the isolated wild type and recombinant enzymes have been determined, and they compare very well (8 μM for the fusion protein; 12 μM for the DEAE partially purified naturally occurring enzyme). Tyrosyl-tRNA synthetase activities have been tested directly in crude extracts obtained by mechanical cell breakage using glass beads (described by S. M. Jazwinski "Preparation of Extracts from Yeast" in "Guide to Protein Purification," by M. P. Deutscher (editor) *Methods in Enzymology* volume 182, Academic Press, Inc. (1990)). The cell breakage was followed by preparation of a 100S supernatant (by an initial low speed spin at 17,000 rpm for 30 min), to remove cell debris and glass beads, followed by a high speed spin at 36,500 rpm for 1 hour (100,000 g) by ultracentrifugation in a 70Ti rotor. However, the TyrRS activity is more stable if the 100S supernatant is purified by a DEAE column. Elution was done with 500 mM NaCl or potassium phosphate, using a gradient or a step-wise elution. Fractions containing TyrRS activity were pooled and concentrated, and stored at −20° C. in 40% glycerol. Activity has remained stable over an 8 month period.

Preparation of 100S supernatant

A single colony of the *Candida albicans* strain ATCC Accession No. 90028 was grown in YEPD to saturation (30° C., 2 days). 5 μl of this saturated culture was used as inoculum for one liter of YPD broth in a 2 liter flask. Incubation was carried out at 30° C. overnight in a shaking incubator (225 rpm). Log-phase cells ($OD_{600}$=8–10) were harvested by low-speed centrifugation (3,000 rpm for 5 min). The cell pellet was washed (with distilled $H_2O$ or 100 mM Tris, pH 7.4) and resuspended as a 40% cell paste in chilled buffer A (20 mM $KPO_4$, pH 7.4 or 20 mM NaCl, pH 8.0, 10% glycerol, 5 mM DTT and 1–2 "Complete" tablets (a cocktail of protease inhibitors from Boehringer-Mannheim)). Cells were broken after addition of an equal volume of glass beads (0.45 micron in diameter; Biospecs) in a Bead-Beater (Biospecs) with 1 min pulses and 1 min cooling periods at 40° C. Total breakage time varied depending on the efficiency of lysis. The 100S supernatant was collected after two centrifugation steps; the conductivity and pH of the supernatant were adjusted before application onto the DEAE column (DEAE Sepharose Fast Flow (Pharmacia LKB Biotechnology)).

Aminoacylation assays

Aminoacylation reactions were carried out at 25° C. in 30 mM HEPES pH 7.5, 30 mM KCl, 5 mM $MgCl_2$, 10 mM DTT, 20 μM [$^3$H]amino acid, 90 μM brewer's yeast tRNA (Boehringer-Mannheim Biochemicals, Inc.), 2 mM ATP, 10 mM KF, and a suitable dilution of the partially purified enzyme from *C. albicans*. For each time point, 15 μl of each reaction were quenched in a 96-well filter plate (Millipore, cat# MAFBNOB50) prefilled with 100 μl of cold 5% TCA. The liquid in the filter plate was drained by applying vacuum suction on the manifold. The plate was subsequently washed 2 times with 200 μl 5% TCA, 2 times with 100 μl double distilled $H_2O$ with continuous vacuum suction, and once with 100 μl EtOH. The plate was heat-dried under vacuum, 100 μl Microscint was added to each well, and the aminoacylated tRNA was quantitated by scintillation counting in a TopCount (Packard) counter. A typical result of a time course aminoacylation assay is shown in FIG. 7.

EXAMPLE 10

Assays for Inhibitors of Enzymatic Activity

Biochemical assay

The extent of aminoacylation of tRNA with tyrosine catalyzed by tyrosyl-tRNA synthetase enzyme from *C. albicans* was measured by monitoring the incorporation of [$^3$H]tyrosine into tRNA. Aminoacylation reactions in the absence of test compounds were measured as control activity, reactions with known inhibitors were employed to assess the sensitivity of the system, and reactions containing test compounds were used to identify novel inhibitors.

Tyrosyl-tRNA synthetase enzyme produced from the pC$^3$695 plasmid and purifed as in Example 7A (specific activity 3.4×105 pmol/min/mg) was used at a 1:10,000 dilution (2.5 nM) pre-incubated at 25° C. with 50 mM HEPES (pH 7.5), 0.05 mg/ml bovine serum albumin, 10 mM dithiothreitol, and 2.5% dimethyl sulfoxide (DMSO) with or without a test or control compound, in 20 μl volumes in the wells of a microtiter plate (Falcon tissue culture plate, #3077). After 30 minutes, the pre-incubation mixture was supplemented to a final concentration in the assay of 5 mM magnesium chloride, 150 mM potassium chloride, 0.3 mM ATP, 5 μM [$^3$H]tyrosine (4 Ci/mmol), 90 μM crude brewer's yeast tRNA and 1.4% DMSO to a final volume of 35 microliters and incubated at 25° C. A 15 microliter aliquot was removed at 6 minutes and 12 minutes and added to an individual well of a Millipore filtration plate (MultiScreen-FB, MAFB NOB 10) containing 100 microliters of cold 5% (wt/vol) trichloroacetic acid. Trichloroacetic acid-precipitable [$^3$H]tyrosine-tRNA was collected by filtration on a Millipore MultiScreen filtration station. Filtration plates were washed two times with 5% trichloroacetic acid, twice with water, and dried overnight. Radioactivity was quantitated with Packard Microscint-20 in a Packard TopCount microplate scintillation counter. Inhibitor activity was reported as a percentage of the control aminoacylation activity, as shown in Table 5 below. CB239 is a known inhibitor used as a positive control.

TABLE 5

| Compound ID | Concentration in assay (μM) | cmp | % activity |
|---|---|---|---|
| none | 0 | 9874 | 100 |
| CB-239 | .2 | 84 | 0.85 |
| CB-239 | .02 | 490 | 5.0 |
| CB-239 | .002 | 4246 | 43 |
| CB-239 | .0002 | 9034 | 91 |
| CB-26387 | 100 | 140 | 1.4 |
| CB-26387 | 100 | 160 | 1.6 |
| CB-26387 | 10 | 1553 | 16 |
| CB-26387 | 1 | 7760 | 79 |
| no compound-control | 0 | 4227 | 100 |
| CB-26359 | 100 | 310 | 7 |
| CB-26359 | 20 | 804 | 19 |
| CB-26359 | 4 | 3496 | 83 |
| CB-26359 | 0.8 | 3783 | 89 |

Whole cell antimicrobial screening

Compounds were tested for antimicrobial activity against *C. albicans* according to standard procedures described by the National Committee for Clinical Laboratory Standards (NCCLS document M27-P, Vol. 12, No. 25, 1992). Compounds were dissolved in 100% dimethyl sulfoxide and were diluted to the final reaction concentrations of 50 μg/ml, 25 μg/ml, 12.5 μg/ml and 6.25 μg/ml in RPMI 1690 media (Sigma; see Pfaller, M. A. et al., *Antimicrob. Agents Chemother.* 30:418–422 (1986)). In all cases, the final concentration of dimethyl sulfoxide incubated with cells is less than or equal to 1%. For minimum inhibitory concentration (MIC) calculations, 2-fold dilutions of compounds were added to wells of a Nunc microwell plate (#62162) containing 5×10$^4$ fungal cells (ATCC Accession No. 10231 and ATCC Accession No. 90028) in a final volume of 100 microliters of RPMI 1690 media. Plates were incubated overnight at 350° C., and optical densities (as a measure of cell growth) were measured using a Molecular Devices SpectraMax 250 plate reader. The MIC value is defined as the lowest compound concentration inhibiting growth of the test organism.

| Strain | Test Compound | MIC |
|---|---|---|
| ATCC #10231 | CB-026359 | 25 µg/ml |
| ATCC #90028 | CB-026359 | 25 µg/ml |

Equivalents

Those skilled in the art will be able to recognize, or be able to ascertain, using no more than routine experimentation, many equivalents to the specific embodiments of the invention described herein. Such equivalents are intended to be encompassed by the following claims.

SEQUENCE LISTING ( 1 ) GENERAL INFORMATION:

( i i i ) NUMBER OF SEQUENCES: 41

( 2 ) INFORMATION FOR SEQ ID NO:1:

( i ) SEQUENCE CHARACTERISTICS:
        ( A ) LENGTH: 1430 base pairs
        ( B ) TYPE: nucleic acid
        ( C ) STRANDEDNESS: double
        ( D ) TOPOLOGY: linear ( i i ) MOLECULE TYPE: other nucleic acid ( x i ) SEQUENCE DESCRIPTION: SEQ ID NO:1:

```
TTTTTTTTT   TTATTTTAT   CGATTTCCGA   CTGTGAATCA   TCACAAACTA   TTCAACACAC     60
GATCAGAAAA  GAATCTTGTT  CTTTATTATT   AATTCTTTNT   TCAACTTGTT   TTGTTTGAAT    120
ATATCTCATC  AGTATGACAG  TCATAACGGA   TCCAGTTGAA   CAATATAATT   TAATTACCAA    180
GGGTTTACAA  GAAACTCTCA  ATGGGCAAAT   CATTAAAGAT   GTTCTAGAAA   AAGAAAATAG    240
ACCAGTTAAA  ATCTATTGGG  GAACAGCACC   AACTGGTAAA   CCACATTGTG   GTTATTTCGT    300
GCCAATGATC  AAATTGGCCC  ATTTCTTAAA   AGCTGGTTGT   GAAGTCACAG   TATTGTTGGC    360
TGATTTGCAT  GCCTTTTTAG  ATAATATGAA   GGCACCATTG   GAAGTTGTCA   AATATCGTGC    420
CAAATACTAT  GAATTTGTTG  TTAAAGCGAT   TTTGAAATCA   ATTAACGTCC   CAATTGAAAG    480
ATTAAAGTTT  GTTGTTGGTT  CCTCATACCA   AAAAGGTGGT   GATTATGTGA   TGGATTTATT    540
TAAATTGTCA  AACATTGTAT  CCCAAAATGA   CGCCAAAAGA   GCTGGTGCTG   ATGTTGTTAA    600
ACAAGTTGCC  AATCCATTAT  TGTCGGGGTT   GATTTATCCA   TTGATGCAAG   CTATAGACGA    660
AGAACATTTG  GGTGTTGATG  CTCAGTTTGG   TGGTGTAGAC   CAAAGAAAGA   TTTTTGTTTT    720
AGCCGAAGAA  AATTTGCCAA  GTATTGGTTA   TAAAAGAGG    GCTCATTTGA   TGAATCCTAT    780
GGTTCCTGGT  TTGGGCCAAG  GTGGTAAGAT   GAGTGCCTCT   GATCCAAACT   CCAAAATTGA    840
TATTATTGAA  GAACCTAAAG  TTGTTAAAAA   GAAGGTCAAT   AGTGCCTACT   GTGCCCCTGG    900
TGAGTTGAAG  GATAATGGGT  TGATTGCATT   TATTGAATAC   GTTATACAAC   CAATTGCTGA    960
ATTGAAGACT  GGTGTTGAAG  GAGCATTCAA   ATTGGATATA   GACAGACCAG   AAAAGTATGG   1020
TGGACCTTTG  TCTTATGACT  CCATCGAACA   ATTAAAGGCT   GACTTTGTGG   ATGGAAAATT   1080
GGCTCCTCCG  GATTTGAAAC  TGGGTGTTGC   TGACAAGATT   AATGAATTGT   TGGCACCAAT   1140
TAGGGCTGAA  TTCGAATCTA  GTGAAGAGTT   TCAAGTGGCA   CAAAAGAATG   GTTACCCAGT   1200
CGAAAAACCA  AAACAAGAAA  AGAAAAAGAA   AGTTAAGAAG   ATAGGTACTA   GATATCCAGG   1260
TACTGTTTCT  GGTGGTGATT  CTGCTGACAC   TCCAGCAAAC   TCTAATGATG   GTGAAAAAGC   1320
TGAAGAAAAG  AAATCTGCAG  AAGAAAAGCC   AACTACTGAA   TAATTTGTAT   AATATTAGAG   1380
CTTCTATAAA  TATATATATC  TGTGTGTATT   TTCAGAAAAT   TAGGTTTTTA                 1430
```

( 2 ) INFORMATION FOR SEQ ID NO:2:

( i ) SEQUENCE CHARACTERISTICS:
        ( A ) LENGTH: 409 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:2:

```
Met Thr Val Ile Thr Asp Pro Val Glu Gln Tyr Asn Leu Ile Thr Lys
 1               5                  10                  15
Gly Leu Gln Glu Thr Leu Asn Gly Gln Ile Ile Lys Asp Val Leu Glu
            20                  25                  30
Lys Glu Asn Arg Pro Val Lys Ile Tyr Trp Gly Thr Ala Pro Thr Gly
        35                  40                  45
Lys Pro His Cys Gly Tyr Phe Val Pro Met Ile Lys Leu Ala His Phe
    50                  55                  60
Leu Lys Ala Gly Cys Glu Val Thr Val Leu Leu Ala Asp Leu His Ala
65                  70                  75                  80
Phe Leu Asp Asn Met Lys Ala Pro Leu Glu Val Val Lys Tyr Arg Ala
                85                  90                  95
Lys Tyr Tyr Glu Phe Val Val Lys Ala Ile Leu Lys Ser Ile Asn Val
            100                 105                 110
Pro Ile Glu Arg Leu Lys Phe Val Val Gly Ser Ser Tyr Gln Lys Gly
        115                 120                 125
Gly Asp Tyr Val Met Asp Leu Phe Lys Leu Ser Asn Ile Val Ser Gln
    130                 135                 140
Asn Asp Ala Lys Arg Ala Gly Ala Asp Val Val Lys Gln Val Ala Asn
145                 150                 155                 160
Pro Leu Leu Ser Gly Leu Ile Tyr Pro Leu Met Gln Ala Ile Asp Glu
                165                 170                 175
Glu His Leu Gly Val Asp Ala Gln Phe Gly Gly Val Asp Gln Arg Lys
            180                 185                 190
Ile Phe Val Leu Ala Glu Glu Asn Leu Pro Ser Ile Gly Tyr Lys Lys
        195                 200                 205
Arg Ala His Leu Met Asn Pro Met Val Pro Gly Leu Gly Gln Gly Gly
    210                 215                 220
Lys Met Ser Ala Ser Asp Pro Asn Ser Lys Ile Asp Ile Ile Glu Glu
225                 230                 235                 240
Pro Lys Val Val Lys Lys Val Asn Ser Ala Tyr Cys Ala Pro Gly
                245                 250                 255
Glu Leu Lys Asp Asn Gly Leu Ile Ala Phe Ile Glu Tyr Val Ile Gln
            260                 265                 270
Pro Ile Ala Glu Leu Lys Thr Gly Val Glu Gly Ala Phe Lys Leu Asp
        275                 280                 285
Ile Asp Arg Pro Glu Lys Tyr Gly Gly Pro Leu Ser Tyr Asp Ser Ile
    290                 295                 300
Glu Gln Leu Lys Ala Asp Phe Val Asp Gly Lys Leu Ala Pro Pro Asp
305                 310                 315                 320
Leu Lys Leu Gly Val Ala Asp Lys Ile Asn Glu Leu Leu Ala Pro Ile
                325                 330                 335
Arg Ala Glu Phe Glu Ser Ser Glu Glu Phe Gln Val Ala Gln Lys Asn
            340                 345                 350
```

-continued

```
Gly  Tyr  Pro  Val  Glu  Lys  Pro  Lys  Gln  Glu  Lys  Lys  Lys  Lys  Val  Lys
          355                 360                      365

Lys  Ile  Gly  Thr  Arg  Tyr  Pro  Gly  Thr  Val  Ser  Gly  Gly  Asp  Ser  Ala
          370                 375                 380

Asp  Thr  Pro  Ala  Asn  Ser  Asn  Asp  Gly  Glu  Lys  Ala  Glu  Glu  Lys  Lys
385                           390                 395                      400

Ser  Ala  Glu  Glu  Lys  Pro  Thr  Thr  Glu
               405
```

(2) INFORMATION FOR SEQ ID NO:3:

(i) SEQUENCE CHARACTERISTICS:
  (A) LENGTH: 26 base pairs
  (B) TYPE: nucleic acid
  (C) STRANDEDNESS: single
  (D) TOPOLOGY: linear (ii) MOLECULE TYPE: other nucleic acid
  (A) DESCRIPTION: /desc = "OLIGONUCLEOTIDE"

(ix) FEATURE:
  (A) NAME/KEY: modified_base
  (B) LOCATION: 3
  (D) OTHER INFORMATION: /mod_base=i (ix) FEATURE:
  (A) NAME/KEY: modified_base
  (B) LOCATION: 6
  (D) OTHER INFORMATION: /mod_base=i (ix) FEATURE:
  (A) NAME/KEY: modified_base
  (B) LOCATION: 15
  (D) OTHER INFORMATION: /mod_base=i (xi) SEQUENCE DESCRIPTION: SEQ ID NO:3:

ACNGGNTTRA TYGGNGAYCC HAGYGG     26

(2) INFORMATION FOR SEQ ID NO:4:

(i) SEQUENCE CHARACTERISTICS:
  (A) LENGTH: 26 base pairs
  (B) TYPE: nucleic acid
  (C) STRANDEDNESS: single
  (D) TOPOLOGY: linear (ii) MOLECULE TYPE: other nucleic acid
  (A) DESCRIPTION: /desc = "OLIGONUCLEOTIDE"

(ix) FEATURE:
  (A) NAME/KEY: modified_base
  (B) LOCATION: 3
  (D) OTHER INFORMATION: /mod_base=i (ix) FEATURE:
  (A) NAME/KEY: modified_base
  (B) LOCATION: 6
  (D) OTHER INFORMATION: /mod_base=i (ix) FEATURE:
  (A) NAME/KEY: modified_base
  (B) LOCATION: 15
  (D) OTHER INFORMATION: /mod_base=i (xi) SEQUENCE DESCRIPTION: SEQ ID NO:4:

ACNGSNAARA TYGGNGAYCC HACHGG     26

(2) INFORMATION FOR SEQ ID NO:5:

(i) SEQUENCE CHARACTERISTICS:
  (A) LENGTH: 31 base pairs
  (B) TYPE: nucleic acid (C) STRANDEDNESS: single
(D) TOPOLOGY: linear (i i) MOLECULE TYPE: other nucleic acid
(A) DESCRIPTION: /desc = "OLIGONUCLEOTIDE"

(i x) FEATURE:
(A) NAME/KEY: modified_base
(B) LOCATION: 6
(D) OTHER INFORMATION: /mod_base=i (i x) FEATURE:
(A) NAME/KEY: modified_base
(B) LOCATION: 18
(D) OTHER INFORMATION: /mod_base=i (i x) FEATURE:
(A) NAME/KEY: modified_base
(B) LOCATION: 21
(D) OTHER INFORMATION: /mod_base=i (i x) FEATURE:
(A) NAME/KEY: modified_base
(B) LOCATION: 24
(D) OTHER INFORMATION: /mod_base=i (x i) SEQUENCE DESCRIPTION: SEQ ID NO:5:

ATRTTNCCCC AYTGRTCNGW NCCNCCRATY T  31

(2) INFORMATION FOR SEQ ID NO:6:

(i) SEQUENCE CHARACTERISTICS:
(A) LENGTH: 31 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "OLIGONUCLEOTIDE"

(i x) FEATURE:
(A) NAME/KEY: modified_base
(B) LOCATION: 6
(D) OTHER INFORMATION: /mod_base=i (i x) FEATURE:
(A) NAME/KEY: modified_base
(B) LOCATION: 18
(D) OTHER INFORMATION: /mod_base=i (i x) FEATURE:
(A) NAME/KEY: modified_base
(B) LOCATION: 21
(D) OTHER INFORMATION: /mod_base=i (i x) FEATURE:
(A) NAME/KEY: modified_base
(B) LOCATION: 24
(D) OTHER INFORMATION: /mod_base=i (x i) SEQUENCE DESCRIPTION: SEQ ID NO:6:

ATRTTNCCRT AYTGRTCNGW NCCNCCRATY T  31

(2) INFORMATION FOR SEQ ID NO:7:

(i) SEQUENCE CHARACTERISTICS:
(A) LENGTH: 24 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "OLIGONUCLEOTIDE"

(x i) SEQUENCE DESCRIPTION: SEQ ID NO:7:

TTGATCWACW CCAAATTGAC AATC                                                          24

( 2 ) INFORMATION FOR SEQ ID NO:8:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OLIGONUCLEOTIDE"

( x i ) SEQUENCE DESCRIPTION: SEQ ID NO:8:

AAAYTWTATT GGGGWACWGC WCCWACWGG                                                     29

( 2 ) INFORMATION FOR SEQ ID NO:9:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

TCGTCTATAG CTTGCATCAA TG                                                            22

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

GAAGTCACAG TATTGTTGGC                                                               20

( 2 ) INFORMATION FOR SEQ ID NO:11:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

GCCAACAATA CTGTGACTTC                                                               20

( 2 ) INFORMATION FOR SEQ ID NO:12:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

CTATTTTCTT TTTCTAGAAC ATC                                                           23

( 2 ) INFORMATION FOR SEQ ID NO:13:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

CTTTAATGAT TTGCCCATTG AGAG 24

(2) INFORMATION FOR SEQ ID NO:14:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:14:

TATGCAATTG CATTTTAGGC AC 22

(2) INFORMATION FOR SEQ ID NO:15:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:15:

ACTCATTTTC ACGCCCTCTA TC 22

(2) INFORMATION FOR SEQ ID NO:16:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:16:

TTGATTGTAG GGGGGTTTGA AGC 23

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:17:

CTTGCGTTCG CCCCGCCAGG 20

(2) INFORMATION FOR SEQ ID NO:18:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:18:

GTAGAGCATC AACTCATTAA CCCAC 25

(2) INFORMATION FOR SEQ ID NO:19:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:19:

AAACATAGGC TTGCAAAATC GCGCT 25

( 2 ) INFORMATION FOR SEQ ID NO:20:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

CCAATACATG GATGAAGATT AC                      22

( 2 ) INFORMATION FOR SEQ ID NO:21:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:21:

ATACCCTTAC TAATGCCCCC TATCG                    25

( 2 ) INFORMATION FOR SEQ ID NO:22:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:22:

GATAGTGGTA GCACCTTTAA GGCGG                    25

( 2 ) INFORMATION FOR SEQ ID NO:23:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:23:

TAATCGCTCT AAAATTTGCT GCTC                     24

( 2 ) INFORMATION FOR SEQ ID NO:24:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:24:

CGCGGATCCG ATCCAGTTGA ACAATATAAT TTAATTACC          39

( 2 ) INFORMATION FOR SEQ ID NO:25:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:25:

CGCGGATCCA TGTCCTCTGC TGCCACGGTT GATCCAGTTG AACAATATAA TTTAATTACC    60

( 2 ) INFORMATION FOR SEQ ID NO:26:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:26:

CCGCTCGAGC GGTACAAATT ATTCAGTAGT TGGTAACTCA TG    42

( 2 ) INFORMATION FOR SEQ ID NO:27:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:27:

CGCGGATCCT ATGACAGTCA TAACAGATCC AGTTGAACAA TAT    43

( 2 ) INFORMATION FOR SEQ ID NO:28:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:28:

GAATTCCATA TGGACAAGAG ATCCCTGCT GTTGTCTCC    39

( 2 ) INFORMATION FOR SEQ ID NO:29:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:29:

GATCCCGGGG AATCGTGAAA ACGGATTAAG CTATGC    36

( 2 ) INFORMATION FOR SEQ ID NO:30:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:30:

CGCGGATCCC GTCAATTAGA GTATGCGGTT ATGGATG    37

( 2 ) INFORMATION FOR SEQ ID NO:31:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:31:

CGCGGATTCG ACCAACGAGA TTGCCACGAA ACTAGAGG    38

( 2 ) INFORMATION FOR SEQ ID NO:32:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:32:

CGGGGTACCG AAGGAGGGGC AAAGAAAGCA GGATGC 36

( 2 ) INFORMATION FOR SEQ ID NO:33:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( x i ) SEQUENCE DESCRIPTION: SEQ ID NO:33:

CATCAGCAAC GGACATATTG G 21

( 2 ) INFORMATION FOR SEQ ID NO:34:

( i ) SEQUENCE CHARACTERISTICS:
( A ) LENGTH: 32 base pairs
( B ) TYPE: nucleic acid
( C ) STRANDEDNESS: single
( D ) TOPOLOGY: linear ( x i ) SEQUENCE DESCRIPTION: SEQ ID NO:34:

CCAAGAAGCT TGAAGTAATA ATAGGCGCAT GC 32

( 2 ) INFORMATION FOR SEQ ID NO:35:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( x i ) SEQUENCE DESCRIPTION: SEQ ID NO:35:

CGTACTGCAG GATTGTATGC TTGGTATAGC 30

( 2 ) INFORMATION FOR SEQ ID NO:36:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( x i ) SEQUENCE DESCRIPTION: SEQ ID NO:36:

GGAATTCTGA AAACAACTCA TATAAATACG 30

( 2 ) INFORMATION FOR SEQ ID NO:37:

( i ) SEQUENCE CHARACTERISTICS:
( A ) LENGTH: 32 base pairs
( B ) TYPE: nucleic acid
( C ) STRANDEDNESS: single
( D ) TOPOLOGY: linear ( x i ) SEQUENCE DESCRIPTION: SEQ ID NO:37:

GAGGCGCCCT CTTATCAATC CCTCCTCAA CC 32

( 2 ) INFORMATION FOR SEQ ID NO:38:

( i ) SEQUENCE CHARACTERISTICS:
( A ) LENGTH: 33 base pairs ( B ) TYPE: nucleic acid
( C ) STRANDEDNESS: single
( D ) TOPOLOGY: linear ( x i ) SEQUENCE DESCRIPTION: SEQ ID NO:38:

AAGGGGTACC CCTTATTCAG TAGTTGGCTT TTC    33

( 2 ) INFORMATION FOR SEQ ID NO:39:

( i ) SEQUENCE CHARACTERISTICS:
( A ) LENGTH: 409 amino acids
( B ) TYPE: amino acid
( C ) STRANDEDNESS:
( D ) TOPOLOGY: linear ( x i ) SEQUENCE DESCRIPTION: SEQ ID NO:39:

| Met | Thr | Val | Ile | Thr | Asp | Pro | Val | Glu | Gln | Tyr | Asn | Leu | Ile | Thr | Lys |
| 1   |     |     |     | 5   |     |     |     |     | 10  |     |     |     |     | 15  |     |
| Gly | Leu | Gln | Glu | Thr | Leu | Asn | Gly | Gln | Ile | Ile | Lys | Asp | Val | Leu | Glu |
|     |     |     | 20  |     |     |     |     | 25  |     |     |     |     | 30  |     |     |
| Lys | Glu | Asn | Arg | Pro | Val | Lys | Ile | Tyr | Trp | Gly | Thr | Ala | Pro | Thr | Gly |
|     |     | 35  |     |     |     |     | 40  |     |     |     |     | 45  |     |     |     |
| Lys | Pro | His | Cys | Gly | Tyr | Phe | Val | Pro | Met | Ile | Lys | Leu | Ala | His | Phe |
|     | 50  |     |     |     |     | 55  |     |     |     |     | 60  |     |     |     |     |
| Leu | Lys | Ala | Gly | Cys | Glu | Val | Thr | Val | Leu | Leu | Ala | Asp | Leu | His | Ala |
| 65  |     |     |     |     | 70  |     |     |     |     | 75  |     |     |     |     | 80  |
| Phe | Leu | Asp | Asn | Met | Lys | Ala | Pro | Leu | Glu | Val | Val | Lys | Tyr | Arg | Ala |
|     |     |     |     | 85  |     |     |     |     | 90  |     |     |     |     | 95  |     |
| Lys | Tyr | Tyr | Glu | Phe | Val | Val | Lys | Ala | Ile | Leu | Lys | Ser | Ile | Asn | Val |
|     |     |     | 100 |     |     |     |     | 105 |     |     |     |     | 110 |     |     |
| Pro | Ile | Glu | Arg | Leu | Lys | Phe | Val | Val | Gly | Ser | Ser | Tyr | Gln | Lys | Gly |
|     |     | 115 |     |     |     |     | 120 |     |     |     |     | 125 |     |     |     |
| Gly | Asp | Tyr | Val | Met | Asp | Leu | Phe | Lys | Leu | Ser | Asn | Ile | Val | Ser | Gln |
|     | 130 |     |     |     |     | 135 |     |     |     |     | 140 |     |     |     |     |
| Asn | Asp | Ala | Lys | Arg | Ala | Gly | Ala | Asp | Val | Val | Lys | Gln | Val | Ala | Asn |
| 145 |     |     |     |     | 150 |     |     |     |     | 155 |     |     |     |     | 160 |
| Pro | Leu | Leu | Ser | Gly | Leu | Ile | Tyr | Pro | Leu | Met | Gln | Ala | Ile | Asp | Glu |
|     |     |     |     | 165 |     |     |     |     | 170 |     |     |     |     | 175 |     |
| Glu | His | Leu | Gly | Val | Asp | Ala | Gln | Phe | Gly | Gly | Val | Asp | Gln | Arg | Lys |
|     |     |     | 180 |     |     |     |     | 185 |     |     |     |     | 190 |     |     |
| Ile | Phe | Val | Leu | Ala | Glu | Glu | Asn | Leu | Pro | Ser | Ile | Gly | Tyr | Lys | Lys |
|     |     | 195 |     |     |     |     | 200 |     |     |     |     | 205 |     |     |     |
| Arg | Ala | His | Leu | Met | Asn | Pro | Met | Val | Pro | Gly | Leu | Gly | Gln | Gly | Gly |
|     | 210 |     |     |     |     | 215 |     |     |     |     | 220 |     |     |     |     |
| Lys | Met | Ser | Ala | Ser | Asp | Pro | Asn | Ser | Lys | Ile | Asp | Ile | Ile | Glu | Glu |
| 225 |     |     |     |     | 230 |     |     |     |     | 235 |     |     |     |     | 240 |
| Pro | Lys | Val | Val | Lys | Lys | Lys | Val | Asn | Ser | Ala | Tyr | Cys | Ala | Pro | Gly |
|     |     |     |     | 245 |     |     |     |     | 250 |     |     |     |     | 255 |     |
| Glu | Leu | Lys | Asp | Asn | Gly | Leu | Ile | Ala | Phe | Ile | Glu | Tyr | Val | Ile | Gln |
|     |     |     |     | 260 |     |     |     |     | 265 |     |     |     |     | 270 |     |
| Pro | Ile | Ala | Glu | Leu | Lys | Thr | Gly | Val | Glu | Gly | Ala | Phe | Lys | Leu | Asp |
|     |     | 275 |     |     |     |     | 280 |     |     |     |     | 285 |     |     |     |
| Ile | Asp | Arg | Pro | Glu | Lys | Tyr | Gly | Gly | Pro | Leu | Ser | Tyr | Asp | Ser | Ile |
|     |     | 290 |     |     |     |     | 295 |     |     |     |     | 300 |     |     |     |
| Glu | Gln | Leu | Lys | Ala | Asp | Phe | Val | Asp | Gly | Lys | Leu | Ala | Pro | Pro | Asp |
| 305 |     |     |     |     | 310 |     |     |     |     | 315 |     |     |     |     | 320 |

|         |       |       |       |       |       |       |       |       |       |       |       |       |       |       |
|---------|-------|-------|-------|-------|-------|-------|-------|-------|-------|-------|-------|-------|-------|-------|
| Leu | Lys | Ser | Gly | Val<br>325 | Ala | Asp | Lys | Ile | Asn<br>330 | Glu | Leu | Leu | Ala | Pro<br>335 | Ile |
| Arg | Ala | Glu | Phe<br>340 | Glu | Ser | Ser | Glu | Glu<br>345 | Phe | Gln | Val | Ala | Gln<br>350 | Lys | Asn |
| Gly | Tyr | Pro<br>355 | Val | Glu | Lys | Pro | Lys<br>360 | Gln | Glu | Lys | Lys | Lys<br>365 | Val | Lys |
| Lys | Ile<br>370 | Gly | Thr | Arg | Tyr | Pro<br>375 | Gly | Thr | Val | Ser | Gly<br>380 | Gly | Asp | Ser | Ala |
| Asp<br>385 | Thr | Pro | Ala | Asn | Ser<br>390 | Asn | Asp | Gly | Glu | Lys<br>395 | Ala | Glu | Glu | Lys | Lys<br>400 |
| Ser | Ala | Glu | Glu | Lys<br>405 | Pro | Thr | Thr | Glu |

( 2 ) INFORMATION FOR SEQ ID NO:40:

( i ) SEQUENCE CHARACTERISTICS:
        ( A ) LENGTH: 224 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:40:

```
GGTGAAGATG  TTGGAATTTT  TGGCTASATA  TGGTAGACAT  ATTAGAGTTA  GTTCGATGTT      60
AGCACGTGAT  TCCATTCAAT  CAAGATTAGA  ACTGGGTGGA  ATTGGATTCA  ATGAATTTAC     120
CTATCAGATT  CTACAAGCTT  ATGATTTTTG  GCATTTATAC  AAGGATGAAA  ATGTTAATAT     180
GCAAATYGGV  GGBAYBGACC  AATRBGGYAA  TATAATCCAT  ATGA                      224
```

( 2 ) INFORMATION FOR SEQ ID NO:41:

( i ) SEQUENCE CHARACTERISTICS:
        ( A ) LENGTH: 74 amino acids
        ( B ) TYPE: amino acid
        ( C ) STRANDEDNESS: Not Relevant
        ( D ) TOPOLOGY: linear ( i i ) MOLECULE TYPE: peptide ( i x ) FEATURE:
        ( A ) NAME/KEY: Modified-site
        ( B ) LOCATION: 1..74
        ( D ) OTHER INFORMATION: /note= "Translation of Base Pairs
        2-223 of SEQ ID NO:40"

( x i ) SEQUENCE DESCRIPTION: SEQ ID NO:41:

|         |       |       |       |       |       |       |       |       |       |       |       |       |       |       |
|---------|-------|-------|-------|-------|-------|-------|-------|-------|-------|-------|-------|-------|-------|-------|
| Val<br>1 | Lys | Met | Leu | Glu<br>5 | Phe | Leu | Ala | Xaa | Tyr<br>10 | Gly | Arg | His | Ile | Arg<br>15 | Val |
| Ser | Ser | Met | Leu<br>20 | Ala | Arg | Asp | Ser | Ile<br>25 | Gln | Ser | Arg | Leu | Glu<br>30 | Leu | Gly |
| Gly | Ile | Gly<br>35 | Phe | Asn | Glu | Phe | Thr<br>40 | Tyr | Gln | Ile | Leu | Gln<br>45 | Ala | Tyr | Asp |
| Phe | Trp<br>50 | His | Leu | Tyr | Lys | Asp<br>55 | Glu | Asn | Val | Asn | Met<br>60 | Gln | Ile | Gly | Gly |
| Xaa<br>65 | Asp | Gln | Xaa | Gly | Asn<br>70 | Ile | Ile | His | Met |

What is claimed is:

1. An isolated nucleic acid which encodes a Candida tyrosyl-tRNA synthetase.

2. The isolated nucleic acid of claim 1, wherein the tyrosyl-tRNA synthetase is a *Candida albicans* tyrosyl-tRNA synthetase.

3. Isolated nucleic acid which encodes tyrosyl-tRNA synthetase having the amino acid sequence of a tyrosyl-tRNA synthetase isolated from a species of Candida, said nucleic acid hybridizing under high stringency conditions to DNA having the sequence SEQ ID NO:1.

4. Isolated nucleic acid having the sequence of a nucleic acid isolated from a species of Candida and encoding a tyrosyl-tRNA synthetase, which hybridizes under high stringency conditions to DNA having the sequence SEQ ID NO:1.

5. Isolated nucleic acid having the sequence of a nucleic acid isolated from a species of Candida, encoding a tyrosyl-tRNA synthetase which shares at least about 95% percent amino acid sequence similarity with a Candida tyrosyl-tRNA synthetase encoded by SEQ ID NO:1.

6. An essentially pure nucleic acid which hybridizes under very high stringency conditions to DNA having SEQ ID NO:1or to an RNA counterpart of SEQ ID NO:1, and encodes at least a functional portion of a Candida tyrosyl-tRNA synthetase, said portion having catalytic activity or binding function.

7. An essentially pure nucleic acid of claim 6 wherein the tyrosyl-tRNA synthetase is a *Candida albicans* tyrosyl-tRNA synthetase.

8. An essentially pure nucleic acid which encodes the amino acid sequence SEQ ID NO:2.

9. An essentially pure nucleic acid which encodes the amino acid sequence SEQ ID NO:39.

10. An isolated nucleic acid vector comprising a nucleic acid which encodes a Candida tyrosyl-tRNA synthetase.

11. An isolated nucleic acid vector of claim 10 wherein the tyrosyl-tRNA synthetase is a *Candida albicans* tyrosyl-tRNA synthetase.

12. (Amended) An isolated nucleic acid vector comprising a nucleic acid which encodes at least a functional portion of a Candida tyrosyl-tRNA synthetase, and which hybridizes to DNA having the sequence SEQ ID NO:1under very high stringency conditions, said portion having catalytic activity or binding function.

13. An isolated nucleic acid vector comprising isolated nucleic acid having the sequence of a nucleic acid isolated from a species of Candida and encoding a tyrosyl-tRNA synthetase, which nucleic acid hybridizes under high stringency conditions to DNA having the sequence SEQ ID NO: 1.

14. An isolated nucleic acid vector comprising nucleic acid which encodes tyrosyl-tRNA synthetase having the amino acid sequence of a tyrosyl-tRNA synthetase isolated from a species of Candida, said nucleic acid hybridizing under high stringency conditions to DNA having the sequence SEQ ID NO: 1.

15. A host cell comprising a recombinant nucleic acid which encodes a Candida tyrosyl-tRNA synthetase.

16. A host cell of claim 15 wherein the Candida tyrosyl-tRNA synthetase is a *Candida albicans* tyrosyl-tRNA synthetase.

17. A host cell comprising a recombinant Candida tyrosyl-tRNA synthetase gene which expresses a Candida tyrosyl-tRNA synthetase or a functional portion thereof, said portion having catalytic activity or binding function.

18. A host cell of claim 17 in which the recombinant Candida tyrosyl-tRNA synthetase gene expresses a *Candida albicans* tyrosyl-tRNA synthetase or a functional portion thereof said portion having catalytic activity or binding function.

19. A host cell comprising isolated nucleic acid having the sequence of a nucleic acid isolated from a species of Candida and encoding a tyrosyl-tRNA synthetase, which nucleic acid hybridizes under high stringency conditions to DNA having the sequence SEQ ID NO:1.

20. An expression vector comprising a nucleic acid encoding a fusion protein comprising a Candida tyrosyl-tRNA synthetase or functional portion thereof having catalytic activity or binding function, wherein said nucleic acid comprises all or part of a coding sequence for a Candida tyrosyl-tRNA synthetase, and wherein the coding sequence is operably linked to one or more expression control sequences.

21. A tester strain comprising a suitable host cell, said host cell comprising a heterologous Candida tyrosyl-tRNA synthetase gene or portion thereof having catalytic activity or binding function, wherein the gene or portion thereof complements a defect in a host gene encoding a tyrosyl-tRNA synthetase.

22. The tester strain of claim 21 in which a host gene encoding a tyrosyl-tRNA synthetase has been lost or has been altered relative to wild type so as to make no gene product, a gene product which is inactive, or a gene product which can be conditionally made inactive.

23. The tester strain of claim 21 in which the host cells are of a genus other than Candida.

24. The tester strain of claim 22 in which the Candida tyrosyl-tRNA synthetase gene or portion thereof is a *Candida albicans* tyrosyl-tRNA synthetase gene or portion thereof having catalytic activity or binding function.

25. A method for producing active Candida tyrosyl-tRNA synthetase or a functional portion thereof comprising:
   a) constructing a recombinant nucleic acid vector comprising a coding sequence for Candida tyrosyl-tRNA synthetase or a portion thereof having catalytic activity or binding function, wherein the coding sequence is under the control of transcription signals and is linked to appropriate translation signals;
   b) introducing the vector into suitable host cells which support the replication of the vector; and
   c) maintaining the host cells under conditions in which Candida tyrosyl-tRNA synthetase is expressed.

26. A method for producing active Candida tyrosyl-tRNA synthetase or a functional portion thereof comprising introducing a recombinant nucleic acid vector comprising a coding sequence for a Candida tyrosyl-tRNA synthetase or a portion thereof having catalytic activity or binding function into suitable host cells, and maintaining the host cells under conditions in which the gene is expressed.

27. A method for producing a Candida tyrosyl-tRNA synthetase or a functional portion thereof comprising maintaining a host cell containing a recombinant nucleic acid encoding a protein comprising a Candida tyrosyl-tRNA synthetase or a functional portion thereof having catalytic activity or binding function under conditions suitable for expression of the nucleic acid, whereby the encoded Candida tyrosyl-tRNA synthetase or functional portion thereof is expressed and thereby produced.

28. The method of claim 27 further comprising the step of isolating the Candida tyrosyl-tRNA synthetase or functional portion thereof.

29. The method of claim 27 wherein the Candida tyrosyl-tRNA synthetase is a *Candida albicans* tyrosyl-tRNA synthetase.

30. Isolated nucleic acid encoding a polypeptide comprising an amino acid sequence selected from the group consisting of SEQ ID NO:2, SEQ ID NO:39, and portions thereof having catalytic activity or binding function.

31. Isolated nucleic acid encoding a polypeptide comprising a Candida tyrosyl-tRNA synthetase or portion thereof having catalytic or binding function.

32. Isolated nucleic acid encoding a polypeptide comprising a *Candida albicans* tyrosyl-tRNA synthetase or portion thereof having catalytic or binding function.

33. A host cell comprising a recombinant nucleic acid encoding a polypeptide comprising a Candida tyrosyl-tRNA synthetase or portion thereof having catalytic activity or binding function.

34. A method for producing a polypeptide comprising a Candida tyrosyl-tRNA synthetase or portion thereof having catalytic activity or binding function comprising maintaining a host cell of claim 33 under conditions suitable for expression of the nucleic acid, whereby the polypeptide is expressed and thereby produced.

35. The method of claim 34 further comprising isolating the polypeptide.

36. A host cell comprising a recombinant nucleic acid encoding a polypeptide comprising a *Candida albicans* tyrosyl-tRNA synthetase or portion thereof having catalytic activity or binding function, wherein said nucleic acid hybridizes under high stringency conditions to DNA having SEQ ID NO:1.

37. A method for producing a polypeptide comprising a *Candida albicans* tyrosyl-tRNA synthetase or portion thereof having catalytic activity or binding function comprising maintaining a host cell of claim 36 under conditions suitable for expression of the nucleic acid, whereby the polypeptide is expressed and thereby produced.

38. The method of claim further comprising isolating the polypeptide.

* * * * *

UNITED STATES PATENT AND TRADEMARK OFFICE
CERTIFICATE OF CORRECTION

PATENT NO. : 5,871,987
DATED : February 16, 1999
INVENTOR(S) : Mandana Sassanfar, Paul L. Gallant, Xiaoyu Shen, Nianjun Tao, Jianshi Tao and Fariba Houman It is certified that error appears in the above-identified patent and that said Letters Patent is hereby corrected as shown below:

Column 67, line 34: Before "An isolated nucleic acid vector", delete -- (Amended)--; and Column 70, line 13: After "The method of", delete the word "claim" and insert therefor --claim 37--.

Signed and Sealed this

Eighth Day of June, 1999

*Attest:*

Q. TODD DICKINSON

*Attesting Officer*  Acting Commissioner of Patents and Trademarks